United States Patent
Itoh et al.

(10) Patent No.: US 7,368,107 B2
(45) Date of Patent: May 6, 2008

(54) TUMOR ANTIGEN PEPTIDES DERIVED FROM CYCLOPHILIN B

(75) Inventors: Kyogo Itoh, Saga-ken (JP); Shinya Gomi, Soja (JP)

(73) Assignee: Dainippon Sumitomo Pharma Co., Ltd., Osaka-shi (JP)

( * ) Notice: Subject to any disclaimer, the term of this patent is extended or adjusted under 35 U.S.C. 154(b) by 186 days.

(21) Appl. No.: 11/227,238

(22) Filed: Sep. 16, 2005

(65) Prior Publication Data

US 2006/0008463 A1    Jan. 12, 2006

Related U.S. Application Data

(62) Division of application No. 09/720,469, filed as application No. PCT/JP99/03360 on Jun. 24, 1999, now Pat. No. 7,041,297.

(30) Foreign Application Priority Data

Jun. 25, 1998    (JP)    ................. 10-178449

(51) Int. Cl.
*A61K 39/00*    (2006.01)

(52) U.S. Cl. ................. 424/93.21; 424/184.1; 435/325

(58) Field of Classification Search ............... None
See application file for complete search history.

(56) References Cited

FOREIGN PATENT DOCUMENTS

| EP | 0326067 A2 | 8/1989 |
|---|---|---|
| EP | 0326067 A3 | 8/1989 |
| JP | 8500106 A | 1/1996 |
| JP | 9151200 A | 6/1997 |

OTHER PUBLICATIONS

Miyake et al., Jun. 1997;157(6):2351-5.*
Lontung, Chao et al., *Journal of Investigative Dermatology*, vol. 102, No. 4, p. 589 (1994), XP001033799.
G. Alkhatib et al., *Immunology*, vol. 92, No. 2, pp. 173-179 (1997), XP001033900.
Shinya Gomi et al., *Journal of Immunology*, vol. 163, pp. 4994-5004 (1999), XP002948569.
Shinchijo et al., *J. Exp. Med.*, vol. 187, No. 3, pp. 277-288 (1998).
E.R. Price et al., Proc. Natl. Acad. Sci., USA, vol. 88, pp. 1903-1907 (1991).

H.G. Rammensee et al., *Immunogenetics*, vol. 41, pp. 178-228 (1995).
H. Schneider et al., *Biochemistry*, vol. 33, pp. 8218-8224 (1994).
Ralph T. Kubo et al., *Journal of Immunology*, vol. 152, p. 3913 (1994).
L. Rivoltini et al., *Journal of Immunology*, vol. 154, pp. 2257-2265 (1995).
A. Kondo et al., *Journal of Immunology*, vol. 155, pp. 4307-4312 (1995).
T. Sudo et al., *Journal of Immunology*, vol. 155, pp. 4749-4756 (1995).
D.D. Kharkevitch et al., *Int. J. Cancer*, vol. 58, pp. 317-323 (1994).
Van Tsai et al., *Journal of Immunology*, vol. 158, pp. 1796-1802 (1997).
John D. Altman et al., *Science*, vol. 274, pp. 94-96 (1996).
Burgess et al., J. of Cell Bio. 111:2129-2138, (1990).
Lazar et al., Molecular and Cellular Biology 8:1247-152, (1988).
Bowie et al., Science, 247:1306-1310, (1990).
Gohara et al., *Jpn. J. Cancer Res.*, vol. 88, pp. 198-402 (1997).
DNA Research 2, pp. 167-174 (1995).
Yotnda et al., *J. Clin. Invest.*, vol. 102, No. 2, pp. 455-462 (1998).
Takahashi et al., *Cellular Immunology*, vol. 178, pp. 162-171 (1997).
KIAA0156 (Genbank Accession No. D63879).
HLA-A2 cDNA (Genbank Accession No. M84379).
Thomson et al., *The Journal of Immunology*, vol. 160, pp. 1717-1723 (1998).
Riott et al., *Immunology*, Fourth Edition, pp. 7, 9-7 and 11 (1996).
Sherman, L.A. et al., *Critical Reviews in Immunol.*, vol. 18, pp. 47-54 (1998).
Lauritzsen et al., *International Journal of Cancer*, vol. 78, pp. 216-222 1998).
Sarma et al., *Journal of Experimental Medicine*, vol. 189, pp. 811-820 (1999).
M. Nakao et al.; *Cancer Research*, vol. 55, pp. 4248-4252. (1955).
S.A. Rosenberg et al., *J. Nat'l. Cancer Inst.*, vol. 86, pp. 1159-1166 (1994).

* cited by examiner

*Primary Examiner*—Misook Yu
(74) *Attorney, Agent, or Firm*—Birch, Stewart, Kolasch & Birch, LLP

(57) ABSTRACT

Tumor antigen peptides derived from cyclophilins or derivatives thereof having the functionally equivalent properties; medicaments, prophylactics, or diagnostics for tumors comprising as an active ingredient such tumor antigen peptides or derivatives thereof, cyclophilins or partial polypeptides thereof, or genes encoding said cyclophilins or partial polypeptides thereof; in vitro use of the above substances for treatment of tumors; and antibodies against the above tumor antigen peptides derived from cyclophilins or derivatives thereof are provided.

4 Claims, 1 Drawing Sheet

TUMOR ANTIGEN PEPTIDES DERIVED FROM CYCLOPHILIN B

This application is a Divisional of application Ser. No. 09/720,469, filed on Dec. 22, 2000 (now U.S. Pat. No. 7,041,297), which is a national phase application, filed under 35 U.S.C. § 371 of PCT International Application No. PCT/JP99/03360, which was filed on Jun. 24, 1999. The entire contents of both of the above-identified applications are hereby incorporated by reference. This application also claims priority under 35 U.S.C. § 119 to Application No. 178449/1998, which was filed in Japan on Jun. 25, 1998.

SEQUENCE LISTING

This application includes ten (10) pages of a Sequence Listing including 44 sequences appended hereto.

TECHNICAL FIELD

The present invention relates to novel tumor antigen peptides derived from a cyclophilin and related substances. More particularly, it relates to tumor antigen peptides derived from cyclophilin B and derivatives thereof having the functionally equivalent properties, and further to medicaments, prophylactics, or diagnostics for tumors that utilize in vivo or in vitro such tumor antigen peptides, derivatives thereof, cyclophilin B polypeptides, or genes therefor.

BACKGROUND ART

It is known that immune system, particularly T cells, plays an important role in tumor elimination by a living body. Indeed, infiltration of lymphocytes exhibiting cytotoxic effects on tumor cells in human tumor foci has been observed (Arch. Surg., 126:200, 1990), and cytotoxic T lymphocytes (CTLs) recognizing autologous tumor cells have been isolated from melanomas without great difficulties (e.g., Immunol. Today, 8:385, 1987; J. Immunol., 138: 989, 1987; and Int. J. Cancer, 52:52, 1992). In addition, the results of clinical treatment of melanomas by transfer of the CTLs recognizing antologous tumor cells also suggest the importance of T cells in tumor elimination (J. Natl. Cancer. Inst., 86:1159, 1994).

Although it had long been unknown about target molecules for CTLs attacking autologous tumor cells, the recent advance in immunology and molecular biology gradually began elucidating such target molecules. Specifically, it has been found that CTL, using the T cell receptors (TCRs), recognizes a complex between a peptide, called tumor antigen peptide, and a major histocompatibility complex class I antigen (MHC class I antigen, and in the case of human, referred to as HLA antigen), and thereby attacks autologous tumor cells.

Tumor antigen peptides are generated by degradation of proteins specific for tumors, that is, tumor antigen proteins in cells with proteasomes, which proteins are intracellularly synthesized. The tumor antigen peptides thus generated bind to MHC class I antigens (HLA antigens) in endoplasmic reticulum to form complexes and the complexes are transported to the cell surface to be presented as an antigen. A tumor-specific CTL recognizes the complex presented as an antigen, and exhibits anti-tumor effects through its cytotoxic action or production of lymphokines. As a consequence of elucidation of a series of the actions, it has become possible to treat tumors by using tumor antigen proteins or tumor antigen peptides as so-called cancer vaccines to enhance tumor-specific CTLs in the body of a tumor patient.

As a tumor antigen protein, T. Boon et al. identified a protein named MAGE from human melanoma cells for the first time in 1991 (Science, 254:1643, 1991). Subsequently, several additional tumor antigen proteins have been identified mainly from melanoma cells. Examples of melanoma antigens that have been identified are melanosomal proteins such as a melanocytic tissue-specific protein, gp100 (J. Exp. Med., 179:1005, 1994), MART-1 (Proc. Natl. Acad. Sci. USA, 91:3515, 1994), and tyrosinase (J. Exp. Med., 178:489, 1993), MEGE-related proteins that are expressed not only on melanomas but also on various cancer cells and normal testicular cells (J. Exp. Med., 179:921, 1994), β-catenin having a tumor-specific amino acid mutation (J. Exp. Med., 183:1185, 1996), and CDK4 (Science, 269:1281, 1995). Tumor antigen proteins other than those from melanomas have also been identified, including products of oncogenes such as HER2-neu (J. Exp. Med., 181:2109, 1995) and p53 (Proc. Natl. Acad. Sci. USA, 93:14704, 1996), tumor markers such as CEA (J. Natl. Cancer Inst., 87:982, 1995) and PSA (J. Natl. Cancer Inst., 89:293, 1997), and viral proteins such as HPV (J. Immunol., 154:5934, 1995) and EBV (Int. Immunol., 7:653, 1995). Detailed descriptions of these subjects can be found in published reviews (e.g. Immunol. Today, 18:267, 1997; J. Exp. Med., 183:725, 1996; and Curr. Opin. Immunol., 8:628, 1996).

In applications of a tumor antigen protein or tumor antigen peptide to treatment or diagnosis of tumors, it is important to identify a tumor antigen that can be widely used for epithelial tumors such as gastric and lung cancers which occur at a much higher incidence compared to melanomas. In this relation, the present inventors conducted cloning of a gene encoding a novel tumor antigen protein from squamous carcinoma cells derived from esophageal cancer, and identified for the first time from tumor cells other than melanomas several tumor antigen peptides that are bound to and presented on HLA antigens of which HLA types are HLA-A24 or HLA-A26 (J. Exp. Med., 187:277, 1998; International Patent Publication WO 97/46676).

When these tumor antigen peptides are clinically applied in practice, it is desirable to use two or more different tumor antigen peptides rather than to use only a single peptide. That is to say, taking into consideration the facts that all cancer cells do not express an identical tumor antigen in common and that two or more different tumor antigen peptides are presented on a single cancer cell, a treatment using two or more different tumor antigen peptides is believed to be more effective. Indeed, in the case of melanoma, development of cocktail formulations comprising two or more peptides has been attempted, since a single peptide derived from a tumor antigen failed to exhibit adequate effects (Int. J. Cancer, 66:162, 1996; and Int. J. Cancer, 67:54, 1996). Under such circumstances, it is being required to identify novel tumor antigen proteins and tumor antigen peptides that can be widely used for epithelial tumors such as gastric and lung cancers which occur at a high incidence.

DISCLOSURE OF THE INVENTION

The present invention aims to provide novel tumor antigen peptides derived from a cyclophilin, and related substances. More particularly, it aims to provide tumor antigen peptides derived from cyclophilin B and derivatives thereof having the functionally equivalent properties as well as medicaments, prophylactics, and diagnostics for tumors that utilize in vivo or in vitro the tumor antigen peptides, the derivatives thereof, cyclophilin B polypeptides, or genes therefor.

The cyclophilin B-derived tumor antigen peptide of the present invention comprises a tumor antigen peptide that is bound to and presented on HLA-A24 and HLA-A2, which are the HLA antigens that the Japanese and Caucasians carry with a high probability, and it is also a tumor antigen peptide that can be applied to treatment or prophylaxis of a wide range of tumors including epithelial tumors such as lung cancer, bladder cancer, and osteosarcoma, and leukemias. Accordingly, cyclophilin B, the tumor antigen protein of the present invention, and a gene therefor, or tumor antigen peptides derived from cyclophilin B are expected to be useful as novel antitumor medicaments.

In order to obtain novel tumor antigen peptides and a tumor antigen protein from which said peptides are derived, the present inventors made the following attempts.

From lymphocytes of a patient with lung adenocarcinoma, the present inventors firstly established a CTL cell line that recognizes HLA-A24 or HLA-A2-positive bladder cancer, lung cancer, osteosarcoma, or leukemia cell lines, and named it KG-CTL (deposit number: FERM BP-6725).

Next, a cDNA library was prepared from bladder cancer cell line HT-1376 with which the above KG-CTL reacts strongly, and COS-7 cells were doubly transfected with a recombinant plasmid of the library and a recombinant plasmid containing HLA-A2402 (one type of HLA-A24) cDNA. The resulting transfectants were treated with the above KG-CTL, and the amount of produced IFN-γ was measured to determine whether or not KG-CTL was activated. As a result of such screening repeatedly conducted, the present inventors finally succeeded in cloning a gene encoding a tumor antigen protein. Base sequencing of the gene revealed that said tumor antigen protein had the same amino acid sequence as that of a known protein, cyclophilin B.

Cyclophilin B is known to be a binding protein for an immunosuppressive agent, cyclosporin A, and to participate in activation of immunocytes. However, it has never been known prior to the present invention that it has a function as a tumor antigen.

Then, the present inventors identified tumor antigen peptide portions in the amino acid sequence of cyclophilin B that are bound to and presented on HLA-A24 and HLA-A2, and demonstrated that activity as a tumor antigen peptide resides in such peptides and derivatives thereof.

Furthermore, the present inventors demonstrated that homologs of cyclophilin B, cyclophilins A, C, and D, also have tumor antigen peptide activities similar to cyclophilin B.

The present invention has been completed on the basis of the findings as described above.

Thus, the present invention relates to:
(1) a tumor antigen peptide that is a partial peptide derived from a cyclophilin, and that is capable of binding to an HLA antigen and being recognized by cytotoxic T lymphocytes, or a derivative thereof having the functionally equivalent properties;
(2) a tumor antigen peptide that is a partial peptide derived from cyclophilin B, and that is capable of binding to an HLA antigen and being recognized by cytotoxic T lymphocytes, or a derivative thereof having the functionally equivalent properties;
(3) the tumor antigen peptide according to the above (1) or (2) wherein the HLA antigen is HLA-A24 or HLA-A2, or a derivative thereof having the functionally equivalent properties;
(4) the tumor antigen peptide according to the above (3), that is selected from sequences comprising all or part of an amino acid sequence shown in any one of SEQ ID NOs: 1-36 or SEQ ID NOs: 41-43, or a derivative thereof having the functionally equivalent properties;
(5) the tumor antigen peptide according to the above (4), that is selected from sequences comprising all or part of the amino acid sequence shown in SEQ ID NO: 1 or 2, or a derivative thereof having the functionally equivalent properties;
(6) the tumor antigen peptide derivative according to the above (4), that is selected from sequences comprising all or part of an amino acid sequence in which the amino acid residue at position 2 and/or the C-terminus in the amino acid sequence shown in any one of SEQ ID NOs: 1-36 is substituted by another amino acid residue;
(7) the tumor antigen peptide derivative according to the above (6), that is selected from sequences comprising all or part of an amino acid sequence in which the amino acid residue at position 2 and/or the C-terminus in the amino acid sequence shown in SEQ ID NO: 1 or 2 is substituted by another amino acid residue;
(8) the tumor antigen peptide derivative according to the above (6), that is selected from sequences comprising all or part of an amino acid sequence in which the amino acid residue at position 2 in the amino acid sequence shown in any one of SEQ ID NOs: 1-11 is substituted by tyrosine, phenylalanine, methionine, or tryptophan, and/or the amino acid residue at the C-terminus is substituted by phenylalanine, leucine, isoleucine, tryptophan, or methionine;
(9) the tumor antigen peptide derivative according to the above (6), that is selected from sequences comprising all or part of an amino acid sequence in which the amino acid residue at position 2 in the amino acid sequence shown in any one of SEQ ID NOs: 12-36 is substituted by leucine, methionine, valine, isoleucine, or glutamine, and/or the amino acid residue at the C-terminus is substituted by valine or leucine;
(10) the tumor antigen peptide derivative according to the above (8), that is selected from sequences comprising all or part of the amino acid sequence shown in SEQ ID NO: 37 or 38;
(11) the tumor antigen peptide derivative according to the above (10), that is selected from sequences comprising all or part of the amino acid sequence shown in SEQ ID NO: 39 or 40;
(12) a pharmaceutical composition for treating or preventing tumors, that comprises as an active ingredient at least one of substances selected from tumor antigen peptides and derivatives thereof according to any one of the above (1)-(11);
(13) a pharmaceutical composition for treating or preventing tumors, that comprises as an active ingredient a cyclophilin, a partial polypeptide of the cyclophilin that comprises a tumor antigen peptide portion capable of binding to an HLA antigen and being recognized by cytotoxic T lymphocytes, or a gene encoding the cyclophilin or the partial polypeptide thereof;
(14) a pharmaceutical composition for treating or preventing tumors, that comprises as an active ingredient cyclophilin B, a partial polypeptide of cyclophilin B that comprises a tumor antigen peptide portion capable of binding to an HLA antigen and being recognized by cytotoxic T lymphocytes, or a gene encoding the cyclophilin B or the partial polypeptide thereof;

(15) an antibody that specifically binds to the tumor antigen peptide or the derivative thereof according to any one of the above (1)-(11);

(16) an antigen-presenting cell wherein a complex between an HLA antigen and the tumor antigen peptide or the derivative thereof according to any one of the above (1)-(11) is presented on the surface of a cell having antigen-presenting ability that is isolated from a tumor patient;

(17) an antigen-presenting cell on which a complex between an HLA antigen and a tumor antigen peptide derived from a cyclophilin is presented, said antigen-presenting cell being prepared by allowing a cell having antigen-presenting ability isolated from a tumor patient to be incorporated with the cyclophilin, a partial polypeptide thereof that comprises the tumor antigen peptide portion capable of binding to the HLA antigen and being recognized by cytotoxic T lymphocytes, or a gene encoding the cyclophilin or the partial polypeptide thereof;

(18) an antigen-presenting cell on which a complex between an HLA antigen and a tumor antigen peptide derived from cyclophilin B is presented, said antigen-presenting cell being prepared by allowing a cell having antigen-presenting ability isolated from a tumor patient to be incorporated with cyclophilin B, a partial polypeptide of cyclophilin B that comprises the tumor antigen peptide portion capable of binding to the HLA antigen and being recognized by cytotoxic T lymphocytes, or a gene encoding the cyclophilin B or the partial polypeptide thereof;

(19) a pharmaceutical composition for treating tumors, that comprises as an active ingredient the antigen-presenting cell according to any one of the above (16)-(18);

(20) a cytotoxic T lymphocyte that specifically recognizes a complex between an HLA antigen and a tumor antigen peptide or derivative thereof according to any one of the above (1)-(11);

(21) a cytotoxic T lymphocyte that specifically recognizes a complex between an HLA antigen and a tumor antigen peptide or derivative thereof, that is presented on an antigen-presenting cell according to any one of the above (16)-(18);

(22) a pharmaceutical composition for treating tumors, that comprises as an active ingredient the cytotoxic T lymphocyte according to the above (20) or (21);

(23) a cytotoxic T lymphocyte of which deposit number is FERM BP-6725;

(24) a method for identifying tumor antigen proteins or tumor antigen peptides, which comprises using KG-CTL according to the above (23); and

(25) a diagnostic agent for tumors that comprises as an active ingredient a tumor antigen peptide or a derivative thereof according to any one of the above (1)-(11).

The present invention is based on our first demonstration that substances called cyclophilins have an activity as a tumor antigen protein. Although the present invention is described below in detail with reference to cyclophilin B as an embodiment of the present invention, the following descriptions are not restricted to cyclophilin B and, also relate to the other known cyclophilins, that is, cyclophilins A, C, and D (*Biochemistry*, 3, 8218, 1994).

In the present invention, the term "tumor antigen peptide" refers to a partial peptide that comprises a part of cyclophilin B and is capable of binding to an HLA antigen and being recognized by CTL. Accordingly, any peptide falls within the scope of tumor antigen peptide of the present invention, regardless of its length or its position in the amino acid sequence of cyclophilin B, as long as the peptide comprises a part of the amino acid sequence of human cyclophilin B, which is registered in WWW Entrez databases as a GenBank Accession No. M60857 and is described in *Proc. Natl. Acad. Sci. U.S.A.*, 88:1903-1907, 1991, and a complex between said peptide and an HLA antigen is capable of being recognized by CTL. Such tumor antigen peptides of the present invention can be identified by synthesizing a candidate peptide which comprises a part of cyclophilin B and conducting an assay for determining whether or not a complex between the candidate peptide and an HLA antigen is recognized by CTL, in other words, whether or not the candidate peptide has an activity as a tumor antigen peptide.

In this connection, synthesis of peptides may be conducted according to a method usually used in peptide chemistry. Examples of such known methods are those described in the literatures including "Peptide Synthesis", Interscience, New York, 1966; "The Proteins", vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

Methods for identifying tumor antigen peptides of the present invention are further described below.

The respective sequence rules (motifs) of antigen peptides that are bound to and presented on the following HLA types have been known; HLA-A1, -A0201, -A0204, -A0205, -A0206, -A0207, -A11, -A24, -A31, -A6801, -B7, -B8, -B2705, -B37, -Cw0401, and -Cw0602 (see, e.g., *Immunogenetics*, 41:178, 1995). Regarding the motif for HLA-A24, for example, it is known that in the sequence of peptides consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152: 3913, 1994; *Immunogenetics*, 41:178, 1995; *J. Immunol.*, 155:4307, 1994). Likewise, the motifs shown in the following Table 1 are known for HLA-A2 (*Immunogenetics*, 41:178, 1995; *J. Immunol.*, 155:4749, 1995).

TABLE 1

| Type of HLA-A2 | Amino acid at the second position from N-terminus | Amino acid at C-terminus |
|---|---|---|
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

(the peptides are 8-11 amino acids in length)

By analysis of antigen peptides bound to various HLA molecules (*Immunogenetics*, 41:178, 1995), it has been shown that the length of the peptides is usually about 8 to 14 amino acids long, although antigen peptides of 14 or more amino acids in length are also observed for HLA-DR, -DP, and -DQ.

It is easy to select peptide portions involved in such motifs from the amino acid sequence of cyclophilin B. That is, such peptide portions involved in the above motif structures can be easily selected by inspecting the amino acid sequence of cyclophilin B. Tumor antigen peptides of the present invention can be then identified by synthesizing candidate peptides thus selected, according to a method described above and conducting an assay for determining whether or not a complex between the candidate peptide and an HLA antigen is recognized by CTL, in other words, whether or not the candidate peptide has an activity as a tumor antigen peptide.

A specific example of the method for identifying tumor antigen peptides of the present invention is a method described in *J. Immunol.*, 154:2257,1995. Specifically, peripheral blood lymphocytes are isolated from a human who is positive for the type of an HLA antigen that is expected to present the candidate peptide, and are stimulated in vitro by adding the candidate peptide. If the candidate induces CTL that specifically recognizes the HLA-antigen-presenting cells pulsed with the candidate peptide, it is indicated that the candidate peptide may function as a tumor antigen peptide. In this connection, the presence or absence of CTL induction can be detected, for example, by measuring the amount of various cytokines (for example, IFN-γ) produced by CTL in response to the antigen peptide-presenting cells using, for example, an ELISA method. Alternatively, a method in which the cytotoxicity of CTL against antigen peptide-presenting cells labeled with $^{51}$Cr is measured ($^{51}$Cr release assay, *Int. J. Cancer*, 58:317, 1994) may also be used for such detection.

Furthermore, the above detection can also be achieved as follows. An expression plasmid expressing a cDNA for the type of an HLA antigen that is expected to present the candidate peptide is introduced into, for example, COS-7 cells (ATCC No. CRL1651) or VA-13 cells (RIKEN CELL BANK, The Institute of Physical and Chemical Research), and the resultant cells are pulsed with the candidate peptide. The cells are then treated with the CTLs as describe above, and the amount of various cytokines (for example, IFN-γ) produced by said CTLs is measured (*J. Exp. Med.*, 187:277, 1998).

Specific examples of various assays as described above are illustrated below in Examples 7, 10, and 12 hereinafter.

Cyclophilin B contains HLA-A24- or HLA-A2-restricted tumor antigen peptide portions. In order to identify HLA-A24-restricted tumor antigen peptides, HLA-A24 cDNA (*Cancer Res.*, 55:4248-4252, GenBank Accession No. M64740) can be used as a cDNA encoding the HLA antigen, along with those CTLs that are prepared by peptide-stimulation of human peripheral blood lymphocytes or KG-CTL (FERM BP-6725). Likewise, for HLA-A2-restricted tumor antigen peptides, identification of such tumor antigen peptides can be achieved in a similar manner to that described above except that HLA-A2 cDNA (GenBank Accession No. M84379) is used.

Apart from the above cases wherein the sequence rules (motifs) have been elucidated, in cases wherein a relevant peptide motif is not elucidated like HLA-A26, tumor antigen peptides of the present invention can be identified, for example, according to the method described in WO 97/46676, provided that a CTL line recognizing a complex between HLA-A26 and a tumor antigen peptide is available.

The methods for identifying tumor antigen peptides as described above may be hereinafter collectively referred to as "assay methods for tumor antigen peptides".

As described above, it is known that the sequences of tumor antigen peptides that are bound to and presented on HLA-A24 obey a certain rule (motif), and in particular, the motif is that, in a sequence of a peptide consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152:3913, 1994; *Immunogenetics*, 41:178, 1995; *J. Immunol.*, 155:4307, 1994). Likewise, a similar rule (motif) can be found in the sequences of tumor antigen peptides that are bound to and presented on HLA-A2, and in particular, the motifs shown in the above Table 1 are known (*Immunogenetics*, 41, 178, 1995; *J. Immunol.*, 155:4749, 1995). Accordingly, among tumor antigen peptides of the present invention, HLA-A24- and HLA-A2-restricted tumor antigen peptides are exemplified by those tumor antigen peptides that are partial peptides involved in such motif structures in the amino acid sequence of cyclophilin B and that are capable of binding to respective HLA antigens and being recognized by CTLs.

Particular examples of HLA-A24-restricted tumor antigen peptides described above are those tumor antigen peptides that comprises all or part of an amino acid sequence shown in any one of SEQ ID NOs: 1-11 and that are capable of binding to an HLA-A24 antigen and being recognized by CTL. Likewise, particular examples of HLA-A2-restricted tumor antigen peptides are those tumor antigen peptides that comprises all or part of an amino acid sequence shown in any one of SEQ ID NOs: 12-36 and that are capable of binding to an HLA-A2 antigen and being recognized by CTL.

Thus, examples of tumor antigen peptides of the present invention include:
1) peptides that consists of an amino acid sequence shown in any one of SEQ ID NOs: 1-36,
2) peptides that comprise the full length of an amino acid sequence shown in any one of SEQ ID NOs: 1-36 and that are elongated in the N-terminal and/or C-terminal direction as compared to said amino acid sequence, or peptides that consists of a consecutive portion of an amino acid sequence shown in any one of SEQ ID NOs: 1-36, said peptides being capable of binding to respective HLA antigens and being recognized by CTLs. In this context, the peptides in the above 2) may be about 8-11 amino acids in length in view of the fact that they are bound and presented by respective HLA antigens.

Suitable examples of HLA-A24-restricted tumor antigen peptides of the present invention include those tumor antigen peptides that comprise all or part of the amino acid sequence shown in SEQ ID NO: 1 or 2 and that are capable of binding to an HLA-A24 antigen and being recognized by CTL. Thus, examples are:
1) peptides that consists of the amino acid sequence shown in SEQ ID NO: 1 or 2,
2) peptides that comprise the full length of the amino acid sequence shown in SEQ ID NO: 1 or 2 and that are elongated in the N-terminal and/or C-terminal direction as compared to said amino acid sequence, or peptides that consists of a consecutive portion of the amino acid sequence shown in SEQ ID NO: 1 or 2, said peptides being capable of binding to HLA-A24 antigens and being recognized by CTLs. In this context, the peptides in the above 2) may be about 8-11 amino acids in length in view of the fact that they are bound to and presented on HLA-A24 antigens.

In the present invention, the term "derivative having properties functionally equivalent to those of a tumor antigen peptide" (hereinafter may be simply referred to as tumor antigen peptide derivative) refers to an altered peptide of which the amino acid sequence contains alteration of one or more, preferably one to several, amino acid residues of an amino acid sequence of a tumor antigen peptide of the present invention, and which has the properties as a tumor antigen peptide, that are to be capable of binding to an HLA antigen and being recognized by CTL. Accordingly, all altered peptides fall within the scope of tumor antigen peptide of the present invention so long as they contains alteration of one or more amino acid residues of an amino acid sequence of a tumor antigen peptide of the present invention, and have the properties as tumor antigen peptides, that is, are capable of binding to HLA antigens and being recognized by CTLs.

In this context, "alteration" of an amino acid residue means substitution, deletion and/or addition (including addition of amino acids to the N-terminus and/or the C-terminus of the peptide) of an amino acid residue, with substitution of an amino acid residue being preferred. For alterations involving substitution of an amino acid residue, although the number and the position of amino acid residues to be substituted may be determined arbitrarily so long as the activity as a tumor antigen peptide is retained, it is preferred that one to several residues are substituted since tumor antigen peptides are usually about 8 to 14 amino acids in length as described above.

A preferred length of tumor antigen peptide derivatives of the present invention is about 8 to 14 amino acids as in case of the tumor antigen peptide described above, although derivatives of 14 or more amino acids long may also be possible for HLA-DR, -DP, and -DQ.

Such tumor antigen peptide derivatives of the present invention can be identified by synthesizing altered peptides that contain alteration of a part of a tumor antigen peptide of the present invention in accordance with the above preparation of peptide, and by conducting the above assay for tumor antigen peptides.

As described above, the sequence rules (motifs) for peptides that are bound to and presented on HLA types such as HLA-A1, -A0201, -A0204, -A0205, -A0206, -A0207, -A11, -A24, -A31, -A6801, -B7, -B8, -B2705, -B37, -0w0401, and -Cw0602 have been elucidated. Consequently, tumor antigen peptide derivatives containing alteration of one or more amino acids in a tumor antigen peptide of the present invention can be prepared on the basis of such motifs.

For example, regarding the motif for antigen peptides that are bound to and presented on HLA-A24, it is known as described above that in the sequence of a peptide consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152: 3913, 1994; *Immunogenetics*, 41:178, 1995; *J. Immunol.*, 155:4307, 1994). Likewise, the motifs shown in the above Table 1 are known for HLA-A2. In addition, amino acid residues having properties similar to those of amino acids according to the motifs may also be accepted. Therefore, examples of tumor antigen peptide derivatives of the present invention include those peptide derivatives that comprise all or part of an amino acid sequence in which one or more amino acid residues at any positions that may be allowed for substitution according to the motifs (for HLA-A24 and HLA-A2, position 2 and the C-terminus) are substituted by other amino acids, and which derivatives have activity of binding to HLA antigens and being recognized by CTLs. Preferred examples are those tumor antigen peptide derivatives that comprise all or part of an amino acid sequence in which substitution of amino acid residues are selected from that of amino acid residues at said positions according to the above motifs, and which derivatives have the above activity. A preferred length of "all or part" of an amino acid sequence is about 8 to 14 amino acids, although it might be a length of 14 or more amino acids for HLA-DR, -DP, and -DQ.

Examples of HLA-A24- or HLA-A2-restricted tumor antigen peptide derivatives include those peptide derivatives that comprise all or part of an amino acid sequence in which one or more amino acid residues at positions that are allowed for substitution according to the above motifs, specifically, at position 2 and/or the C-terminus, of a peptide derived from the amino acid sequence of cyclophilin B having a binding motif for HLA-A24 or HLA-A2 are substituted by other amino acid residues, and which derivatives have the above activity. Preferred examples are those tumor antigen peptide derivatives that comprise all or part of an amino acid sequence in which the amino acid residues at position 2 and/or the C-terminus are substituted by amino acid residues according to the above motifs, and which derivatives have the above activity. In such HLA-A24- or HLA-A2-restricteid tumor antigen peptide derivatives, a preferred length of "all or part" of the amino acid sequence is about 8 to 11 amino acids.

In particular, examples are those tumor antigen peptide derivatives that comprise all or part of an amino acid sequence in which the amino acid residues at position 2 and/or the C-terminus of an amino acid sequence shown in any one of SEQ ID NOs: 1 to 36 are substituted by other amino acid residues and which derivatives have the above activity. Preferred examples are those tumor antigen peptide derivatives that comprise all or part of an amino acid sequence in which the amino acid residues at position 2 and/or the C-terminus of an amino acid sequence shown in any one of SEQ ID NOs: 1 to 36 are substituted by amino acid residues according to the above motifs and which derivatives have the above activity. Specifically, examples of HLA-A24-restricted tumor antigen derivatives are those tumor antigen peptide derivatives that comprise all or part of an amino acid sequence in which the amino acid residue at position 2 of an amino acid sequence shown in any one of SEQ ID NOs: 1 to 11 is substituted by tyrosine, phenylalanine, methionine, or tryptophan and/or the amino acid residue at the C-terminus is substituted by phenylalanine, leucine, isoleucine, tryptophan, or methionine and which derivatives have the above activity. Likewise, examples of HLA-A2-restricted tumor antigen derivatives are those tumor antigen peptide derivatives that comprise all or part of an amino acid sequence in which the amino acid residue at position 2 of an amino acid sequence shown in any one of SEQ ID NOs: 12 to 36 is substituted by leucine, methionine, valine, isoleucine, or glutamine and/or the amino acid residue at the C-terminus is substituted by valine or leucine and which derivatives have the above activity.

Suitable examples of HLA-A24-restricted tumor antigen peptide derivatives of the present invention are those tumor antigen peptide derivatives that comprise all or part of an amino acid sequence in which the amino acid residues at position 2 and/or the C-terminus of the amino acid sequence shown in SEQ ID NO: 1 or 2 are substituted by other amino acid residues and which derivatives have the above activity. More preferred examples are those tumor antigen peptide derivatives that comprise all or part of an amino acid sequence in which one or more amino acid residues are substituted according to the above motifs, that is, all or part of the amino acid sequence shown in SEQ ID NO: 37 or 38 and which derivatives have the above activity. Suitable examples of such tumor antigen peptide derivatives are shown in SEQ ID NOs: 39 and 40.

Furthermore, as described above, besides cyclophilin B described above, homologs of cyclophilin B, cyclophilins A, C, and D, are also tumor antigen proteins generating tumor antigen peptides. Specific examples of such tumor antigen peptides include HLA-A24-restricted tumor antigen peptides such as SEQ ID NO: 41 (cyclophilin A), SEQ ID NO: 42 (cyclophilin C), and SEQ ID NO: 43 (cyclophilin D).

A tumor antigen peptide or its derivative of the present invention can be used for a pharmaceutical composition for treating or preventing tumors as follows.

When used with the aim of treating or preventing tumors, at least one of, or a combination of two or more of, tumor antigen peptides or their derivatives of the present invention is administered to a patient, if necessary, in combination with other agents such as other tumor antigen peptides. When the composition for treating or preventing tumors which comprises as an active ingredient a tumor antigen peptide or its derivative of the present invention is administered to a cyclophilin B-positive patient, the tumor antigen peptide or derivative thereof is presented at a high density with an HLA antigen of antigen-presenting cells, and therefore, CTLs specific for the presented HLA antigen complex proliferates and destroys the tumor cells. As a result, the tumor of the patient may be treated, or proliferation or metastasis of the tumor may be prevented. Furthermore, the composition for treating or preventing tumors comprising as an active ingredient a tumor antigen peptide or its derivative of the present invention can achieve an increased therapeutic effect by its combined use with a chemotherapy or radiotherapy.

The composition for treating or preventing tumors comprising as an active ingredient a tumor antigen peptide or its derivative of the present invention may be administered along with an adjuvant in order to effectively establish the cellular immunity, or may be administered in a particulate dosage form. For such purpose, those adjuvants described in the literature (*Clin. Microbiol. Rev.*, 7:277-289, 1994) are applicable. In addition, liposomal preparations, particulate preparations in which the ingredient is bound to beads having a diameter of several μm, or preparations in which the ingredient is attached to lipids are also possible. Administration may be achieved, for example, intradermally, hypodermically, or by intravenous injection. Although the amount of a tumor antigen peptide or its derivative of the present invention in the formulation to be administered may be adjusted as appropriate depending on, for example, the disease to be treated, the age and the body weight of the particular patient, it is usually preferred to administered 0.0001 mg to 1000 mg, preferably 0.001 mg to 1000 mg, and more preferably 0.1 mg to 10 mg every several days to every several months.

Furthermore, cyclophilin B protein from which tumor antigen peptides of the present invention are derived or a gene encoding said cyclophilin B may also be used for a pharmaceutical composition for treating or preventing tumors.

In addition to the full-length cyclophilin B or the full-length gene therefor, any parts thereof, such parts linked together, or even those containing alterations in their base or amino acid sequences can achieve desired treatment or prevention of tumors so long as they comprise at least one of peptide portions that can bind to an HLA antigen and being recognized by CTLs. In this context, those substances that "comprise at least one of peptide portions that can bind to an HLA antigen and being recognized by CTLs" are herein referred to as "partial polypeptides".

When cyclophilin B protein or its partial polypeptide is applied as the composition for treating or preventing tumors, it may be administered in a dosage form, administration mode, and dose similar to the above tumor antigen peptide or derivative thereof. When administered to a tumor patient, cyclophilin B protein or its partial polypeptide is incorporated into antigen-presenting cells, and tumor antigen peptides that are subsequently generated by intracellular degradation bind to HLA antigens to form complexes. The complexes are presented at a high density on the surface of antigen-presenting cells, and CTLs specific for the presented complex efficiently proliferate in the body and destroy the tumor cells. In this manner, treatment or prevention of tumors is achieved.

In order to apply a gene encoding cyclophilin B or its partial polypeptide to a composition for treating or preventing tumors, the following methods may be used.

Administration and introduction of the gene of the present invention into cells may be achieved using viral vectors or according to any one of other procedures (*Nikkei-Science*, April, 1994, pp. 20-45; *Gekkan-Yakuji*, 36(1), 23-48 (1994); *Jikken-Igaku-Zokan*, 12(5), 1994, and references cited therein).

Examples of the methods using viral vectors include those methods in which DNA of the present invention is incorporated into DNA or RNA virus such as retrovirus, adenovirus, adeno-associated virus, herpesvirus, vaccinia virus, poxvirus, poliovirus, or Sindbis virus, and introduced into cells. Among these methods, those using retrovirus, adenovirus, adeno-associated virus, or vaccinia virus are particularly preferred.

Other methods may include those in which expression plasmids are directly injected intramuscularly (DNA vaccination), the liposome method, Lipofectin method, microinjection, the calcium phosphate method, and electroporation, with DNA vaccination and the liposome method being particularly preferred.

In order to allow a gene of the present invention to act as a medicine in practice, one can use either of two methods: an in vivo method in which DNA is directly introduced into the body, or an ex vivo method in which certain cells are removed from human, and after introducing DNA into said cells extracorporeally, the cells are reintroduced into the body (*Nikkei-Science*, April, 1994, pp. 20-45; *Gekkan-Yakuji*, 36(1), 23-48 (1994); *Jikkenn-Igaku-Zokan*, 12(15), 1994; and references cited therein). An in vivo method is more preferred.

In the case of in vivo methods, the gene may be administered by any appropriate route depending on the disease and symptoms to be treated and other factors. For example, it may be administered via intravenous, intraarterial, subcutaneous, intracutaneous, or intramuscular route. In the case of in vivo methods, the compositions may be administered in various dosage forms such as solution, and are typically formulated, for example, in the form of injection containing DNA of the present invention as an active ingredient, to which conventional carriers may also be added, if necessary. If a gene of the present invention is included in liposomes or membrane-fused liposomes (such as Sendai virus (HVJ)-liposomes), the compositions may be in the form of liposome formulations such as suspension, frozen drug, centrifugally-concentrated frozen drug or the like.

Although the amount of a gene of the present invention in such formulations may vary depending on the disease to be treated, the age and weight of the patient, and the like, it is typically preferred to administer 0.0001-100 mg, preferably 0.001-10 mg, of a gene of the present invention every several days to every several months.

By such administration of a gene of the present invention, the tumor antigen protein is highly expressed in antigen-presenting cells. Tumor antigen peptides that are subsequently generated by intracellular degradation bind to HLA antigens to form complexes, and the complexes are densely presented on the cell surface. As a result, CTLs specific for these complexes efficiently proliferate in the body, and destroy tumor cells. In this way, treatment or prevention of proliferation or metastasis of tumors are achieved.

Cyclophilin B, partial polypeptides thereof, and genes encoding such substances that can be used as medicaments as described above may be prepared as follows. A gene encoding cyclophilin B can be easily cloned by preparing appropriate PCR primers on the basis of the base sequence of human cyclophilin B cDNA registered at GenBank under Accession No. M60857 as found by WWW Entrez databases search, and using them to conduct PCR according to the description of a standard text such as "Molecular Cloning", 2nd ed., Cold Spring Harbor Laboratory Press (1989). For this purpose, one may also consult *Proc. Natl. Acad. Sci. U.S.A.* 88:1903, 1991, which is a report concerning cloning of cyclophilin B. Furthermore, a commercially available cyclophilin B cDNA clone (ATCC No. 107758, Designations: HTNAQ10) may be also used. If desired, alteration may be easily made according to a standard text such as the afore-mentioned "Molecular Cloning". Furthermore, expression of cyclophilin B protein using a gene encoding human cyclophilin B thus cloned may be achieved according to many publications and references such as "Molecular Cloning" mentioned above. An expression plasmid which replicates and functions in host cells is constructed by incorporating DNA to be expressed into an appropriate vector (e.g., 6 pSV-SPORT1), in some cases after adding regulatory sequence(s) such as a promoter sequence, which controls transcription (e.g., trp, lac, T7, or SV40 early promoter), upstream to the DNA. The expression plasmid is then introduced into appropriate host cells to obtain transformants. Examples of host cells include, for example, prokaryotes such as *Escherichia coli*, unicellular eukaryotes such as yeast, and cells derived from multicellular eukaryotes such as insects or animals. Gene transfer into host cells may be achieved by the calcium phosphate method, DEAE-dextran method, the electric pulse method, or the like. Transformants cultured in appropriate medium produce the protein of interest. The tumor antigen protein thus obtained may be isolated and purified according to standard biochemical procedures.

It can be determined whether or not cyclophilin B protein, a partial polypeptide thereof, or a gene encoding such substance prepared as described above has activity as a tumor antigen, that is, whether or not tumor antigen peptides capable of binding to an HLA antigen and being recognized by CTL are generated by intracellular degradation of said protein, for example, by a method using gene expression as follows.

First of all, an expression plasmid containing a candidate gene or gene fragment and another expression plasmid containing DNA encoding an HLA antigen are doubly transfected into cells expressing no tumor antigen proteins, such as COS-7 (ATCC CRL 1651) derived from African green monkey kidney, or fibroblast VA-13 (RIKEN CELL BANK, The Institute of Physical and Chemical Research). The transfection may be achieved, for example, by Lipofectin method using Lipofectamine reagent (Gibco BRL). Subsequently, a tumor-responsive CTL that is restricted to the particular HLA antigen used is added, allowed to act on the transfectants, and then the amount of various cytokines (for example, IFN-γ) produced by said CTL in response to the target cells may be measured, for example, by ELISA to determine whether the candidate gene is a DNA encoding a tumor antigen protein. Since cyclophilin B contains HLA-A24- or HLA-A2-restricted tumor antigen peptide portions, for example, HLA-A24 cDNA (*Cancer Res.*, 55:4248-4252 (1995); GenBank Accession No. M64740) or HLA-A2 cDNA (GenBank Accession No. M84379) may be used as the above DNA encoding the HLA antigen, and those CTLs that are prepared from human peripheral blood lymphocytes as well as KG-CTL (FERM BP-6725) may be used as the above CTL.

A specific example of such activity measurement is described below in Example 2.

Antibodies that specifically bind to a tumor antigen peptide of the present invention or a derivative thereof are also included in the present invention. Such antibodies are easily prepared, for example, according to a method described in "Antibodies: A Laboratory Manual", Lane, H. D. et al. eds., Cold Spring Harbor Laboratory Press, New York, 1989. Specifically, antibodies that recognize a tumor antigen peptide or its derivative of the present invention and antibodies that further neutralize its activity may easily be prepared using the tumor antigen peptide or derivative thereof to appropriately immunize an animal in the usual manner. Such antibodies may be used in affinity chromatography, immunological diagnosis, and the like.

Immunological diagnosis for the presence or absence of tumors using said antibody may be conducted by firstly labeling the above antibody as needed, and using it to detect the presence of antigens in a sample (such as blood, tumor tissue) obtained from a patient suspected to have a tumor. In particular, such immunological diagnosis may be selected as appropriate from immunoblotting, radioimmunoassay (RIA), enzyme-linked immunosorbent assay (ELISA), a fluorescent or luminescent assay, and the like.

A tumor antigen peptide, derivative thereof, tumor antigen protein (cyclophilin B), or gene therefor of the present invention may also be used in vitro for treatment of tumor patients as follows.

On usage of a tumor antigen peptide, derivative thereof, tumor antigen protein, or gene therefor in treatment of tumor, it is important to establish an administration method which can efficiently induce specific CTLs in the body of a patient. As one of the means therefor, the present invention provides an antigen-presenting cell which comprises a complex between an HLA antigen and a tumor antigen peptide or its derivative of the present invention, the complex being presented on the surface of a cell having antigen-presenting ability isolated from a tumor patient, and also provides a pharmaceutical composition for treating tumors, that comprises said antigen-presenting cell as an active ingredient.

In this context, the "cell having antigen-presenting ability" is not specifically restricted so long as it is a cell expressing on its cell surface an HLA antigen capable of presenting a tumor antigen peptide or its derivative of the present invention, and dendritic cells, which is reported to have especially high antigen-presenting ability, are preferred. The substance to be added to prepare an antigen-presenting cell of the present invention from the above-mentioned cell having antigen-presenting ability may be tumor antigen peptides or their derivatives of the present invention, as well as the tumor antigen protein, cyclophilin B, and a gene therefor. In order to prepare an antigen-presenting cell of the present invention, not only the full-length cyclophilin B and gene therefor but also its partial polypeptide and a gene therefor may also be used. When used in the form of a protein or gene, it is necessary to be incorporated into cells. In this regard, see the above descriptions for the composition for treating or preventing tumors comprising the gene or protein as an active ingredient.

In order to prepare antigen-presenting cells of the present invention, cells having antigen-presenting ability are isolated from a tumor patient, and pulsed ex vivo with a tumor antigen peptide, a derivative thereof, a tumor antigen protein, or its partial polypeptide of the present invention to form a complex between an HLA antigen and said tumor antigen peptide or derivative thereof (*Cancer Immunol. Immunother.*, 46:82, 1998; *J. Immunol.* 158:1796, 1997; *Cancer Res.*, 59:1184, 1999). When dendritic cells are used, antigen-presenting cells of the present invention may be prepared, for example, by isolating lymphocytes from peripheral blood of a tumor patient using Ficoll method, removing non-adherent cells, incubating adherent cells in the presence of GM-CSF and IL-4 to induce dendritic cells, and incubating and pulsing said dendritic cells with a tumor antigen peptide, tumor antigen protein of the present invention, or the like. For details, see Example 13.

When antigen-presenting cells of the present invention are prepared by introducing a gene encoding a tumor antigen protein or its partial polypeptide of the present invention into the aforementioned cells having antigen-presenting ability, said gene may be in the form of DNA or RNA. In particular, DNA may be used consulting, for example, *Cancer Res.*, 56:5672, 1996 or *J. Immunol.*, 161:5607, 1998, and RNA may be used by consulting, for example, *J. Exp. Med.*, 184:465, 1996.

A pharmaceutical composition for treating tumors which comprises the above antigen-presenting cells as an active ingredient preferably contains physiological saline, phosphate buffered saline (PBS), medium, or the like in order to stably maintain the antigen-presenting cells. It may be administered, for example, intravenously, subcutaneously, or intradermally. By reintroducing such composition for treating tumors which comprises antigen-presenting cells as an active ingredient into the body of the patient, specific CTLs are efficiently induced in the cyclophilin B-positive patient to achieve treatment of the tumor. It should be undisputed that the HLA types need be compatible between the patient and the peptide used. For example, an HLA-A24-restricted tumor antigen peptide or a derivative thereof must be used with an HLA-A24-positive tumor patient.

In addition, another example of in vitro use of a tumor antigen peptide, a derivative thereof, a tumor antigen protein, or a gene therefor according to the present invention is in the following adoptive immunotherapy.

For melanomas, it has been observed that an adoptive immunotherapy wherein tumor infiltrating T cells taken from the patient himself/herself are cultured ex vivo in large quantities, and then returned into the patient, achieves an therapeutic effect (*J. Natl. Cancer. Inst.*, 86:1159, 1994). Likewise, in mouse melanoma, suppression of metastasis has been observed by in vitro stimulation of splenocytes with a tumor antigen peptide TRP-2, thereby proliferating CTLs specific for the tumor antigen peptide, and administering said CTLs into a melanoma-grafted mouse (*J. Exp. Med.*, 185:453, 1997). This resulted from in vitro proliferation of CTL that specifically recognizes the complex between an HLA antigen of antigen-presenting cells and the tumor antigen peptide. Accordingly, a method for treating tumors is believed to be useful, which comprises in vitro stimulation of peripheral blood lymphocytes from a patient using a tumor antigen peptide, a derivative thereof, a tumor antigen protein, or a gene therefor according to the present invention to proliferate tumor-specific CTLs and subsequent return of the CTLs into the patient.

Thus, the present invention provides CTLs that specifically recognize a complex between the HLA antigen and the tumor antigen peptide or derivative thereof, and also provides a pharmaceutical composition for treating tumors which comprises said CTLs as an active ingredient. Such composition preferably contains physiological saline, phosphate buffered saline (PBS), medium, or the like in order to stably maintain CTLs. It may be administered, for example, intravenously, subcutaneously, or intradermally. By reintroducing the composition for treating tumors which comprises CTLs as an active ingredient into the body of the patient, the toxic effect of CTLs against the tumor cells is enhanced in the cyclophilin B-positive patient and thereby destroys the tumor cells to achieve treatment of the tumor.

Tumor antigen proteins, tumor antigen peptides, and derivatives thereof according to the present invention may be also used as an active ingredient of a diagnostic agent for diagnosing tumors. Thus, by using a tumor antigen protein, tumor antigen peptide, or derivative thereof according to the present invention itself as a diagnostic agent to detect the presence of antibodies in a sample (such as blood or a tumor tissue) obtained from a patient suspected to have a tumor, early detection of tumors and diagnosis of recurrence and metastasis are possible. The same procedure can also be used for selection of tumor patients to whom medicines comprising as an active ingredient, for example, a tumor antigen protein or tumor antigen peptide of the present invention can be applied. In particular, such diagnosis may be conducted using immunoblotting, RIA, ELISA, or a fluorescent or luminescent assay.

Furthermore, in recent years, a new detection method has been established for detecting antigen-specific CTLs using a complex between the antigen peptide and an HLA antigen (*Science*, 274:94,1996). Early detection of tumors and diagnosis of reoccurrence or metastasis are possible by subjecting a complex between a tumor antigen peptide or derivative thereof according to the present invention and an HLA antigen to the above detection method, and thereby detecting tumor antigen-specific CTLs. The same procedure can also be used for selection of tumor patients to whom a medicine comprising as an active ingredient, for example, a tumor antigen protein or tumor antigen peptide of the present invention can be applied, or for determination of the therapeutic effect of said medicine. Thus, the present invention also provides a diagnostic agent for tumors comprising as a part of the active ingredient a tumor antigen peptide or derivative thereof according to the present invention.

In particular, such diagnosis may be conducted as follows: a tetramer of a complex between an HLA antigen fluorescently labeled according to the method described in the literature (*Science*, 274:94, 1996) and a tumor antigen peptide is prepared and used to quantitatively determine the antigen peptide-specific CTLs in peripheral blood lymphocytes of a patient suspected to have a tumor using a flow cytometer.

The present invention also provides KG-CTL (deposit number FERM BP-6725) that is CTL established from tumor infiltrating lymphocytes derived from lung adenocarcinoma. KG-CTL has proved to response to HLA-A24- and HLA-A2-positive cancer cells, and also cyclophilin B of the present invention is a tumor antigen protein discovered by using its reactivity to said KG-CTL as an indicator. Therefore, new tumor antigen proteins and tumor antigen peptides may be found as with cyclophilin B by using KG-CTL. For details, see Example 2 below.

BEST MODE FOR CARRYING OUT THE INVENTION

Figure 1:
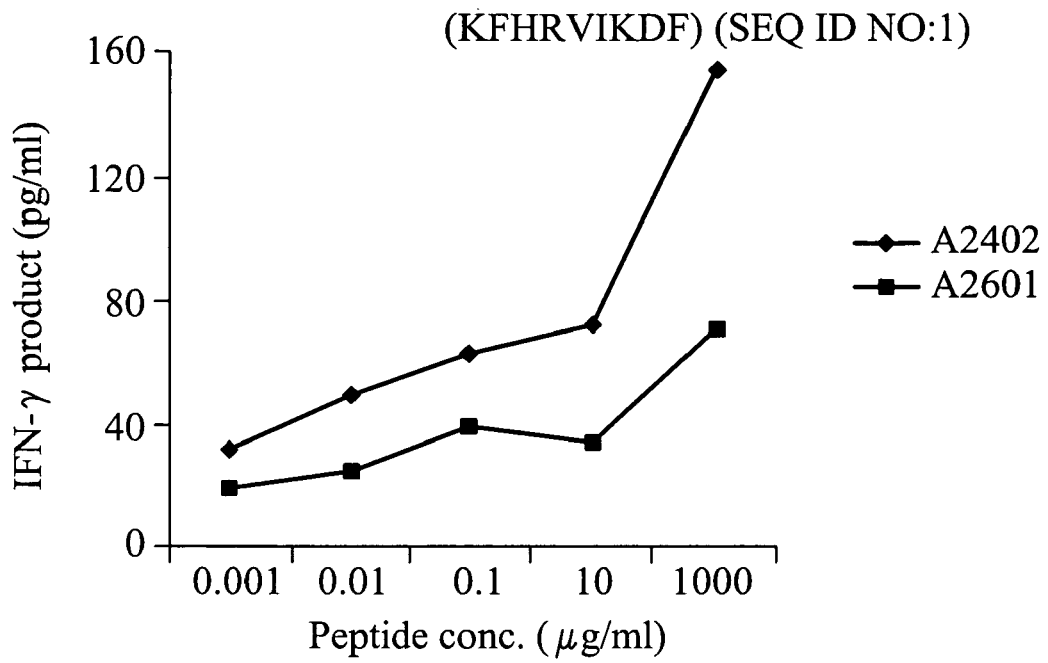
FIG. 1 is a graph indicating the results of measurement wherein COS-7 cells transfected with a recombinant plasmid of HLA-A2402 cDNA or a recombinant plasmid of HLA-A2601 cDNA were co-cultured with KG-CTLs after addition of a tumor antigen peptide of the present invention "84-92 (SEQ ID NO: 1)", and the amount of IFN-γ produced by KG-CTLs was measured. The axis of abscissas indicates the concentration of the peptide added, and the axis of ordinates indicates the amount of IFN-γ produced by KG-CTLs.

The present invention is further illustrated by the following examples, but is not restricted by these examples in any way.

EXAMPLE 1

Establishment of Cytotoxic T Lymphocytes (CTLs) Cell Line from Tumor Infiltrating Lymphocytes (TILs) Derived from Lung Adenocarcinoma A surgical sample taken from a patient with lung adenocarcinoma was divided into small pieces in a culture medium, and the cells were then suspended in a culture medium containing collagenase and DNAase. From the cell suspension, lymphocytes were separated by density centrifugation using Ficoll-Conray solution. The lymphocytes were cultured in a culture medium (hereinafter referred to as lymphocyte medium) consisting of 45% RPMI-1640, 45% AIM-V (Gibco BRL), and 10% FCS supplemented with 100 U/ml interleukin-2 and 0.1 mM NEAA (Gibco BRL). During the first two days of the cultivation, an anti-CD3 antibody NU-T3 (Nichirei Corporation) was added to the culture medium at 1 μg/ml. The cultivation was continued for more than 30 days, and a CTL line that responses to several kinds of HLA-A24- or HLA-A2-positive cancer cell line was thereby established. The CTL line was named KG-CTL, and used in the following experiments. The reactivities of KG-CTL against various cancer cell lines were determined as follows. Cancer cell lines are plated into wells of a 96-well plate at $1 \times 10^4$ cells/well. On the next day, KG-CTLs were added at $1 \times 10^5$ cells/well, further cultured for 18 hours, and the culture medium was then harvested to determine the amount of interferon-γ (IFN-γ) produced by KG-CTLs. Quantitative determination of IFN-γ was conducted by an enzyme immunoassay (ELISA). Specifically, anti-human IFN-γ mouse monoclonal antibody was adsorbed on wells of a 96-well microplate as a solid-phased antibody, and after blocking non-specific bindings with bovine serum albumin, IFN-γ in the sample was allowed to bind to the antibody. An anti-human IFN-γ rabbit polyclonal antibody was then allowed to bind as a detection antibody. After binding of an anti-rabbit immunoglobulin goat antibody labeled with alkaline phosphatase, it was allowed to color using a peroxidase color developing kit T (Sumitomo Bakelite Co.), and the absorbance (405 nm) was then measured. It was compared with values obtained with standard IFN-γ to quantitatively determine the amount of IFN-γ. The reactivities of KG-CTL on various adenocarcinoma cell lines are summarized in Table 2. Likewise, the reactivities of KG-CTL on lymphoid cell lines are shown in Table 3.

TABLE 2

| Adenocarcinoma Cell Line | Amount of IFN-γ Produced by KG-CTL (pg/ml) | HLA-A Type |
|---|---|---|
| HT-1376 (bladder cancer cell line) | 4608 | 2402/2402 |
| 1-87 (lung cancer cell line) | 194 | 0207/1101 |
| 11-18 (lung cancer cell line) | 4632 | 0201/2402 |
| PC-9 (lung cancer cell line) | 1102 | 0206/2402 |
| LC-1 (lung cancer cell line) | 129 | 3101/3302 |
| YT-803 (lung cancer cell line) | 285 | 3101/3302 |
| 143 B (osteosarcoma cell line) | 1547 | 0211/0211 |
| None (only KG-CTL) | 100 | — |

TABLE 3

| Cell Line | Amount of IFN-γ Produced by KG-CTL (pg/ml) | HLA-A Type |
|---|---|---|
| SSB (B cell line[1]) | 5769 | 2402/2402 |
| Ban-B1 (B cell line[1]) | 78 | 3101/3302 |
| HPB-MLT (leukemia cell line) | 189 | 0101/0201 |
| MOLT-16 (leukemia cell line) | 13 | 2301/3002 |
| MT-2 (leukemia cell line) | 3495 | 2402/2402 |
| None (only KG-CTL) | 0 | — |

[1]B cell line obtained by transforming B cells of a healthy donor with EB virus.

The results in Table 2 show that KG-CTL strongly reacts to HLA-A2402-positive cancer cells in the table (HT-1376, 11-18, and PC-9) and produces IFN-γ and that it also reacts to the HLA-A2-positiev cells (143B) and produces IFN-γ. Likewise, the results in Table 3 show that KG-CTL strongly reacts to the HLA-A2402-positive EB-virus-transformed B cell line and a leukemia cell line (SSB and MT-2) and that it also strongly reacts to the HLA-A2-posotive leukemia cell line (HBP-MLT).

The established KG-CTL was deposited at The National Institute of Bioscience and Human Technology, Agency of Industrial Science and Technology (1-1-3 Higashi, Tsukuba, Ibaraki, Japan) (designation of microorganism: KG-CTL; deposition date: Jun. 19, 1998; deposit number: FERM P-16854) (date of conversion to international deposition: May 20, 1999; deposit number: FERM BP-6725). Furthermore, typing of HLA molecules of KG-CTL was conducted by Shionogi & Co. according to the method described in Nakao et al., *Cancer Res.*, 55:4248-4252 (1995), and it was confirmed that the A locus is A0206 and A2402.

EXAMPLE 2

Identification of Tumor Antigen Protein

A cDNA library was prepared from the bladder cancer cell line HT-1376 (ATCC CRL 1472), to which KG-CTL strongly reacted in Example 1, by the following method.

Poly (A)+ mRNA was firstly prepared from HT-1376 by isolation of the total RNA fraction and purification on an oligo (dT) column using a mRNA purification system (Pharmacia Biotech) according to the manufacture's protocol. From the mRNAs, cDNAs having Not I adapter and Sca I adapter linked to each terminus were prepared using SuperScript™ Plasmid System (Gibco BRL) according to the manufacturer's protocol, and then ligated into the cleaved site of an expression vector, plasmid pSV-SPORT1 (Gibco BRL), digested with restriction enzymes Not I and Sal I to yield recombinant plasmids. The recombinant plasmids were introduced into E. coli ElectroMAX DH10B™ cells (Gibco BRL) using electric pulses in Gene Pulser (Bio-Rad), and transformants into which the recombinant plasmids had been introduced were selected in LB medium (1% Bacto-trypton, 0.5% yeast extract, 0.5% NaCl, pH7.3) containing ampicillin (50 μg/ml).

The recombinant plasmid DNAs were recovered from pools of about 100 transformants described above in the following manner. A hundred transformants were introduced and cultured in each well of a 96-well U-bottomed microplate containing LB medium plus ampicillin (50 μg/ml). Part of the culture was then transferred to another 96-well U-bottomed microplate containing 0.25 ml per well of TYGPN medium (F. M. Ausubel et al., "Current Protocols in Molecular Biology", John Wiley & Sons, Inc.), and cultured for 48 hours at 37° C. The remaining cultures in LB medium on the microplate were stored in frozen. Preparation of recombinant plasmid DNAs from transformants cultured in TYGPN medium was achieved on the microplate by the alkaline lysis method (F. M. Ausubel et al., "Current Protocols in Molecular Biology", John Wiley & Sons, Inc.). The recombinant plasmid DNAs recovered by isopropanol precipitation were suspended in 50 μl of 10 mM Tris, 1 mM EDTA, pH 7.4, containing 20 ng/ml RNase.

On the other hand, starting with an esophageal cancer cell line KE-4 deposited at The National Institute of Bioscience and Human Technology, Agency of Industrial Science and Technology (1-1-3 Higashi, Tsukuba, Ibaraki, Japan) (deposition date: May 23, 1997; deposit number: FERM BP-5955), recombinant plasmids were prepared in which cDNAs for HLA-A2402 (GenBank Accession No. M64740) and HLA-A2601 have been incorporated into an expression vector pCR3 (Invitrogen), according to the description in Nakao et al., Cancer Res., 55:4248-4252 (1995).

Subsequently, a cell line derived from African green monkey kidney, COS-7 (ATCC No. CRL1651), was doubly transfected with the recombinant plasmid of HT-1376 cDNA and the recombinant plasmid of HLA-A2402 cDNA using Lipofectin method as follows. Eight thousand COS-7 cells were placed in each well of a 96-well flat-bottomed microplate, and incubated for one day in 100 μl of RPMI 1640 medium containing 10% FCS. Using Lipofectamine reagent (Gibco BRL), 30 μl of a 70-μl mixture consisting of 25 μl of the recombinant plasmid of HT-1376 cDNA corresponding to about 100 transformants, 10 μl (200 ng) of the recombinant plasmid of HLA-A2402 cDNA, and 35 μl of about 50-fold diluted Lipofectin reagent was added in order to doubly transfect the COS-7 cells. Transfectants were prepared in duplicate. After 5 hours, 200 μl of a culture medium containing 10% FCS was added to the transfectants, and further incubated for 48 hours at 37° C. After removing the culture medium, $1.5 \times 10^5$ cells/well of KG-CTL was added, and cultured for 24 hours at 37° C. in 100 μl of a culture medium containing 10% FCS and 25 U/ml IL-2. The culture medium was recovered, and measured for the amount of IFN-γ by the ELISA method described in Example 1.

For those groups that resulted in a high production of IFN-γ, corresponding frozen-stored pools of about 100 transformants transfected with recombinant plasmids of HT-1376 cDNA were used in the further screening as follows. The pools of the transformants were plated on LB agar medium containing ampicillin (50 μg/ml) to obtain colonies. For each group, 400 colonies were cultured as described above so that a single kind of transformant is included in each well, and recombinant plasmid DNAs for HT-1376 cDNA were prepared. Furthermore, in the similar manner to that described above, COS-7 cells were doubly transfected with the recombinant plasmid of HT-1376 cDNA and the recombinant plasmid of HLA-A2402 cDNA followed by co-cultivation with KG-CTL, and IFN-γ produced by KG-CTL in response to the target cells was quantitatively determined in order to select positive plasmids. By these procedures, a HT-1376 cDNA recombinant plasmid clone was selected, and the clone was named 4F2. Furthermore, similar procedures were repeated with 4F2 to determine the amount of IFN-γ produced by KG-CTL. The result is shown below in Table 4.

TABLE 4

| Cells | Amount of IFN-γ Produced by KG-CTL (pg/ml) |
| --- | --- |
| COS-7 + HLA-A2402 | 469 |
| COS-7 + HLA-A2402 + 4F2 | 543 |

When compared to COS-7 cells transfected with only HLA-A2402, KG-CTL reacted more strongly to COS-7 cells doubly transfected with HLA-A2402 and 4F2 and produces more IFN-γ. This result indicated that the protein encoded by 4F2 is a tumor antigen protein.

EXAMPLE 3

Determination of Base Sequence of Tumor Antigen Protein Gene

The base sequence of the plasmid clone 4F2 encoding the tumor antigen protein obtained in Example 2 was determined using DyeDeoxy Terminator Cycle Sequencing kit (Perkin-Elmer). The determined base sequence and the amino acid sequence encoded by the base sequence were compared to known sequences using WWW Entrez databases and it was revealed that the base sequence of the plasmid clone 4F2 corresponds to the amino acid sequence of human cyclophilin B registered as GenBank Accession No. N60857. The sequence of said cyclophilin B is also described in Proc. Natl. Acad. Sci. U.S.A., 88:1903, 1991. Cyclophilin B is a binding protein for an immunosuppressive agent, cyclosporin A, and is known to participate in vivo in activation of immunocytes. It was found by the above Example 2 for the first time that cyclophilin B, of which sole known function had been its participation in immunocyte activation, has a function as a tumor antigen protein.

EXAMPLE 4

Selection of Candidate Peptides

There are certain rules (motifs) in the sequences of antigen peptides bound and presented by HLA antigens. Regarding the motif for HLA-A24, it is known that in the sequence of peptides consisting of 8 to 11 amino acids, the amino acid at position 2 is tyrosine, phenylalanine, methionine, or tryptophan, and the amino acid at the C-terminus is phenylalanine, tryptophan, leucine, isoleucine, or methionine (*Immunogenetics*, 41:178, 1995; *J. Immunol.*, 152:3913, 1994; *J. Immunol.*, 155:4307, 1994). Likewise, it is known for HLA-A2 that the peptides consist of 8 to 11 amino acids and that for HLA-A0201, the amino acid at position 2 is leucine or methionine and the amino acid at the C-terminus is valine or leucine; for HLA-A0204, the amino acid at position 2 is leucine and the amino acid at the C-terminus is leucine; for HLA-A0205, the amino acid at position 2 is valine, leucine, isoleucine, or methionine and the amino acid at the C-terminus is leucine; for HLA-A0206, the amino acid at position 2 is valine or glutamine and the amino acid at the C-terminus is valine or leucine; and for HLA-A0207, the amino acid at position 2 is leucine and the amino acid at the C-terminus is leucine (*Immunogenetics,* 41:178, 1995; *J. Immunol.*, 155:4749, 1995; see also Table 1).

According to such motifs, peptide portions consisting of 8 to 11 peptides having the above motifs were selected from the amino acid sequence of cyclophilin B (GenBank Accession No. M60857), of which function as a tumor antigen protein was found by the present inventors. Selected peptides having a binding motif for HLA-A24 are shown in SEQ ID NOs: 1-11, and peptides having a binding motif for HLA-A2 are shown in SEQ ID NOs: 12-36. These peptides were synthesized at Biologica Co. by the Fmoc method.

Then, $10^4$ COS-7 cells were transfected with a recombinant plasmid of HLA-A2402 cDNA by the Lipofectin method to express HLA-A2402 according to the literature (*J. Exp. Med.*, 187:277, 1998). To these cells, various peptides precedently synthesized that had a binding motif for HLA-A24 were each added at 10 μM for 2 hours in order to pulse the cells. The cells were then co-cultured with $2\times10^4$ KG-CTLs for 18 hours, and the amount of IFN-γ in the culture supernatant produced by KG-CTL was determined by the ELISA method. Subsequently, two peptides, that is, a peptide comprising the sequence from position 84 to position 92 in the amino acid sequence of cyclophilin B (SEQ ID NO: 1, hereinafter sometimes simply referred to as "84-92") and a peptide comprising the sequence from position 91 to position 99 (SEQ ID NO: 2, hereinafter sometimes simply referred to as "91-99") were subjected to the following experiments.

EXAMPLE 5

Synthesis of Lys-Phe-His-Arg-Val-Ile-Lys-Asp-Phe (SEQ ID NO: 1)

Fmoc-Phe-Alko Resin (0.56 mmol/g, 100-200 mesh) was used as a resin in this synthesis. Using 100 mg of this resin, the synthesis was started according to Schedule 1 described below to couple the following residues in order: Fmoc-Asp (OtBu)-OH, Fmoc-Lys(Boc)-OH, Fmoc-Ile-OH, Fmoc-Val-OH, Fmoc-Arg(Pmc)-OH, Fmoc-His (Trt)-OH, Fmoc-Phe-OH, and Fmoc-Lys(Boc)-OH. After the coupling, the procedures were carried out up to Step 3 of Schedule 1 shown below in TALBE 5 to obtain a peptide resin.

To this peptide resin, 2 ml of Reagent K (5% phenol, 5% thioanisole, 5% $H_2O$, and 2.5% ethanedithiol in TFA) was added and allowed to react for 2.5 hours at room temperature. While cooling with ice, 10 ml of diethyl ether was added to the reaction, the mixture was stirred for 10 minutes, filtered, and then washed with 10 ml of diethyl ether. To the filter cake, 10 ml of 10% acetic acid aqueous solution (hereinafter referred to as aqueous acetic acid) was added and the mixture was stirred for 30 minutes. The resin was then filtered, and washed with 4 ml of aqueous acetic acid. After lyophilizing the filtrate and the wash, the crude peptide obtained was dissolved in aqueous acetic acid, and injected into a reverse phase packing material COSMOSIL 5C18-AR column (25ϕ×250 mm) pre-equilibrated with 0.1% aqueous TFA. The column was washed with 0.1% aqueous TFA, and the concentration of acetonitrile was then increased up to 25% over 260 minutes to elute the product at a flow rate of 7 ml/min. The eluate was monitored by A 220 nm. The fractions containing the desired product were combined together and lyophilized to obtain 11.7 mg of Lys-Phe-His-Arg-Val-Ile-Lys-Asp-Phe (SEQ ID NO:1).

The peptide obtained, Lys-Phe-His-Arg-Val-Ile-Lys-Asp-Phe (SEQ ID NO:1), had a retention time of 23.9 minutes in an analysis using a reverse phase packing material YMC-PACK ODS-AM column (4.6ϕ×250 mm) eluted with a linear gradient of acetonitrile concentration from 0 to 60% containing 0.1% TFA, and the results of amino acid analysis and mass spectrometry of the product were consistent with the theoretical values.

Amino Acid Analysis

Hydrolysis: 1% phenol/6N aqueous hydrochloric acid, 110° C., 24 hours;
Analysis method: the ninhydrin method;
Reference amino acid; Theoretical values are indicated in parentheses:
  Asx: 1.01 (1)
  *Val: 1.00 (1)
  Ile: 0.85 (1)
  Phe: 1.94 (2)
  Lys: 1.74 (2)
  His: 0.95 (1)
  Arg: 0.86 (1)

Mass Spectrum (FAB)

$[M+H]^+$: 1190

TABLE 5

Schedule 1

| Step | Duration (min) × the number of treatments |
|---|---|
| 1. (washing) DMF 1.2 ml | 1 × 2 |
| 2. (deprotection) 50% piperidine/DMF | 12 × 1 |
| 3. (washing) DMF 1.2 ml | 1 × 7 |
| 4. (coupling) each amino-protected amino acid (5 equivalents)/NMP solution 0.9 ml, DIC (5 equivalents)/NMP solution 0.3 ml | 30 × 1 |
| 5. (washing) DMF 1.2 ml | 1 × 2 |
| 6. (coupling) each amino-protected amino acid (5 equivalents)/NMP solution 0.9 ml, DIC (5 equivalents)/NMP solution 0.3 ml | 30 × 1 |
| 7. (washing) DMF 1.2 ml | 1 × 4 |

EXAMPLE 6

Synthesis of Asp-Phe-Met-Ile-Gln-Gly-Gly-Asp-Phe (SEQ ID NO: 2)

In the same manner as that described in Example 5, using 100 mg of Fmoc-Phe-Alko Resin, Fmoc-Asp (OtBu)-OH, Fmoc-Gly-OH, Fmoc-Gly-OH, Fmoc-Gln-OH, Fmoc-Ile-OH, Fmoc-Met-OH, Fmoc-Phe-OH, and Fmoc-Asp(OtBu)-OH were coupled in order, and the product was then deprotected. The crude peptide obtained was dissolved in aqueous acetic acid and injected into a reverse phase packing material COSMOSIL 5C18-AR column (25ϕ+×250 mm) pre-equilibrated with 0.1% aqueous TFA. The column was washed with 0.1% aqueous TFA, and the concentration of acetonitrile was then increased up to 31% over 260 minutes to elute the product at a flow rate of 7 ml/min. The eluate was monitored by A 220 nm. The fractions containing the desired product were combined together and lyophilized to obtain 3.6 mg of Asp-Phe-Met-Ile-Gln-Gly-Gly-Asp-Phe (SEQ ID NO:2).

The peptide obtained, Asp-Phe-Met-Ile-Gln-Gly-Gly-Asp-Phe (SEQ ID NO:2), had a retention time of 25.8 minutes in an analysis using a reverse phase packing material YMC-PACK ODS-AM column (4.6ϕ×250 mm) eluted with a linear gradient of acetonitrile concentration from 0 to 60% containing 0.1% TFA, and the results of amino acid analysis (Met being not detected) and mass spectrometry of the product were consistent with the theoretical values.

Amino Acid Analysis

Hydrolysis: 1% phenol/6N aqueous hydrochloric acid, 110° C., 24 hours;
Analysis method: the ninhydrin method;
* Reference amino acid; Theoretical values are indicated in parentheses:
  Asx: 2.02 (2)
  Glx: 1.04 (1)
  Gly: 2.04 (2)
  *Ile: 1.00 (1)
  Phe: 1.97 (2)

Mass Spectrum (FAB):

$[M+H]^+$: 1029

EXAMPLE 7

Identification of Tumor Antigen Pepetide

Figure 2:
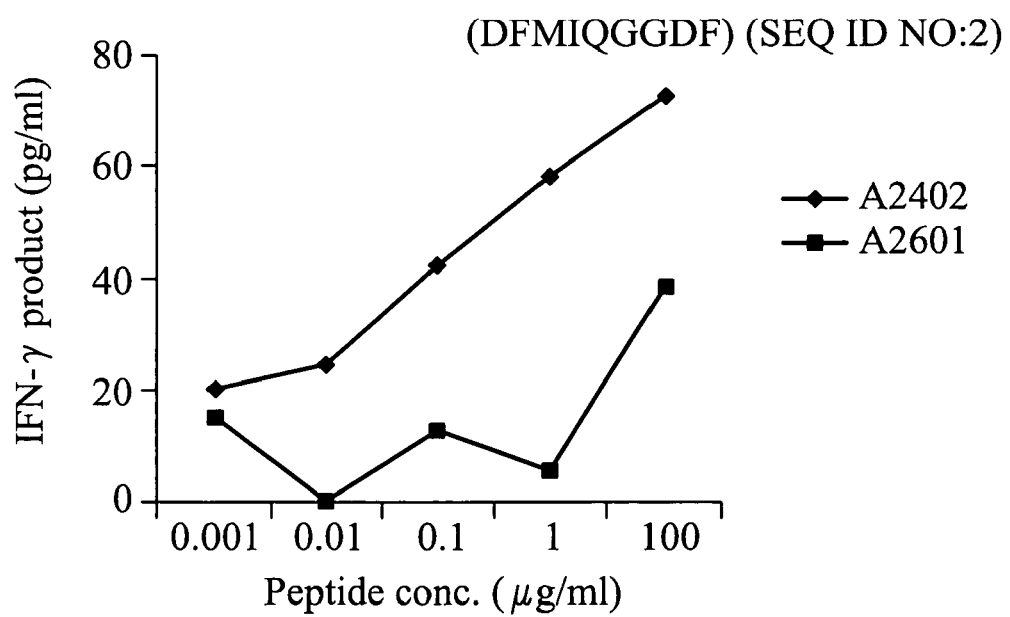
FIG. 2 is a graph indicating the results of measurement wherein COS-7 cells transfected with a recombinant plasmid of HLA-A2402 cDNA or a recombinant plasmid of HLA-A2601 cDNA were co-cultured with KG-CTLs after addition of a tumor antigen peptide of the present invention "91-99 (SEQ ID NO: 2)", and the amount of IFN-γ produced by KG-CTLs was measured. The axis of abscissas indicates the concentration of the peptide added, and the axis of ordinates indicates the amount of IFN-γ produced by KG-CTLs.

An experiment was conducted with two peptides synthesized in the above Examples 5 and 6 in the same manner as that described in Example 4, and it was found that these peptides function as a tumor antigen peptide. The results are shown in FIGS. 1 and 2. In the figures, the axis of abscissas indicates the peptide concentration (pg/ml) and the axis of ordinates indicates the amount of IFN-γ produced by KG-CTLs. When COS-7 cells transfected with a recombinant plasmid of HLA-A2402 cDNA were pulsed with "84-92" and "91-99", the reactivity of KG-CTL was increased in a concentration-dependent manner. As compared to COS-7 cells transfected with a recombinant plasmid of HLA-A2601 cDNA, COS-7 cells transfected with the recombinant plasmid of HLA-A2402 cDNA resulted in a higher reactivity of KG-CTL when pulsed. It was demonstrated by the above results that the two peptides, "84-92" and "91-99", function as an HLA-A24-restricted tumor antigen peptide.

EXAMPLE 8

Synthesis of Lys-Tyr-His-Arg-Val-Ile-Lys-Asp-Phe (SEQ ID NO: 39)

Since it was revealed in Example 7 that "84-92" and "91-99" function as a tumor antigen peptide, two derivatives in which phenylalanine at position 2 is substituted by tyrosine within the scope of the binding motif for HLA-A24, "84-92·2F-Y" (SEQ ID NO: 39) and "91-99·2F-Y" (SEQ ID NO: 40), were prepared.

The peptide Lys-Tyr-His-Arg-Val-Ile-Lys-Asp-Phe (SEQ ID NO: 39) was synthesized in the same manner as that described in Example 5. Specifically, using 100 mg of Fmoc-Phe Alko Resin, Fmoc-Asp (OtBu)-OH, Fmoc-Lys (Boc)-OH, Fmoc-Ile-OH, Fmoc-Val-OH, Fmoc-Arg(Pmc)-OH, Fmoc-His(Trt)-OH, Fmoc-Tyr(tBu)-OH, and Fmoc-Lys (Boc)-OH were coupled in order, and the product was then deprotected. The crude peptide obtained was dissolved in aqueous acetic acid and injected into a reverse phase packing material COSMOSIL 5C18-AR column (25ϕ×250 mm) pre-equilibrated with 0.1% aqueous TFA. The column was washed with 0.1% aqueous TFA, and the concentration of acetonitrile was then increased up to 25% over 200 minutes to elute the product at a flow rate of 7 ml/min. The eluate was monitored by A 220 nm. The fractions containing the desired product were combined together and lyophilized to obtain 44.9 mg of Lys-Try-His-Arg-Val-Ile-Lys-Asp-Phe (SEQ ID NO:39).

The peptide obtained Lys-Tyr-His-Arg-Val-Ile-Lys-Asp-Phe (SEQ ID NO:39) had a retention time of 17.7 minutes in an analysis using a reverse phase packing material YMC-PACK ODS-AM column (4.6ϕ×250 mm) eluted with a linear gradient of acetonitrile concentration from 0 to 60% containing 0.1% TFA, and the results of amino acid analysis and mass spectrometry of the product were consistent with the theoretical values.

Amino Acid Analysis

Hydrolysis: 1% phenol/6N aqueous hydrochloric acid, 110° C., 24 hours;
Analysis method: the ninhydrin method;
* Reference amino acid; Theoretical values are indicated in parentheses:
  Asx: 1.06 (1)
  *Val: 1.00 (1)
  Ile: 0.85 (1)
  Tyr: 0.89 (1)
  Phe: 0.95 (1)
  Lys: 1.85 (2)
  His: 0.98 (1)
  Arg: 0.91 (1).

Mass Spectrum (FAB)

$[M+H]^+$: 1206

EXAMPLE 9

Synthesis of Asp-Tyr-Met-Ile-Gln-Gly-Gly-Asp-Phe (SEQ ID NO: 40)

In the same manner as that described in Example 5, using 100 mg of Fmoc-Phe-Alco Resin, Fmoc-Asp (OtBu)-OH, Fmoc-Gly-OH, Fmoc-Gly-OH, Fmoc-Gln-OH, Fmoc-Ile-OH, Fmoc-Met-OH, Fmoc-Tyr(tBu)-OH, and Fmoc-Asp (OtBu)-OH were coupled in order, and the product was then deprotected. The crude peptide obtained was dissolved in aqueous acetic acid and injected into a reverse phase packing material COSMOSIL 5C18-AR column (25ϕ×250 mm) pre-equilibrated with 0.1% aqueous TFA. The column was washed with 0.1% aqueous TFA, and the concentration of acetonitrile was then increased up to 27% over 200 minutes to elute the product at a flow rate of 7 ml/min. The eluate was monitored by A 220 nm. The fractions containing the desired product were combined together and lyophilized to obtain 12.8 mg of Asp-Tyr-Met-Ile-Gln-Gly-Gly-Asp-Phe (SEQ ID NO:40).

The peptide obtained Asp-Tyr-Met-Ile-Gln-Gly-Gly-Asp-Phe (SEQ ID NO:40) had a retention time of 24.7 minutes in an analysis using a reverse phase packing material YMC-PACK ODS-AM column (4.6φ×250 mm) eluted with a linear gradient of acetonitrile concentration from 0 to 60% containing 0.1% TFA, and the results of amino acid analysis (Met being not detected) and mass spectrometry of the product were consistent with the theoretical values.

Amino Acid Analysis

Hydrolysis: 1% phenol/6N aqueous hydrochloric acid, 110° C., 24 hours;
Analysis method: the ninhydrin method;
* Reference amino acid; Theoretical values are indicated in parentheses:
  Asx: 2.04 (2)
  Glx: 1.02 (1)
  Gly: 2.06 (2)
  *Ile: 1.00 (1)
  Tyr: 0.82 (1)
  Phe: 0.98 (1)

Mass Spectrum (FAB)

$[M+H]^+$: 1045

EXAMPLE 10

Induction of CTL from Peripheral Blood Lymphocytes by Tumor Antigen Peptides and Derivatives thereof The inventors investigated whether antigen-specific CTLs can be induced from peripheral blood lymphocytes using the peptide "84-92" (SEQ ID NO: 1) synthesized in Example 5 and the peptide "84-92·2F-Y" (SEQ ID NO: 39) synthesized in Example 8.

Lymphocytes were separated from peripheral blood of a leukemia patient who was heterozygous for A24 in the HLA-A locus using Ficoll method. The lymphocytes were placed into wells of a 24-well plate at $2\times10^6$ cells/well, and cultured in the lymphocyte medium. The above tumor antigen peptides were added to the culture medium at 10 μM to stimulate the peripheral blood lymphocytes. After one week, the above tumor antigen peptide was added to attain 10 μM together with about $2\times10^5$ cells of X-radiated (50 Gy) peripheral blood lymphocytes for the second stimulation. After additional one week, the third stimulation was conducted in a similar manner. Cultured lymphocytes were harvested one week after the third stimulation. Using as target cells ($1\times10^4$ cells) BEC-2, which is an HLA-A2402-positive EB virus-transformed B cell line expressing the tumor antigen protein of the present invention (cyclophilin B), and Ban-B1, which is an HLA-A2402-negative EB virus-transformed B cell line expressing the tumor antigen protein of the present invention, the amount of IFN-γ in the culture medium produced by the above lymphocytes ($8\times10^4$ cells) in response to the target cells was measured by ELISA. The results are shown in Table 6.

TABLE 6

| Antigen Peptide | IFN-γ in Supernatant (pg/ml) | |
|---|---|---|
| | BEC-2 | Ban-B1 |
| "84-92" | 383 | 38 |
| "84-92 · 2F-Y" | 489 | 63 |
| None | 245 | 74 |

Another experiment similar to that described above was further conducted using "91-99" (SEQ ID NO: 2) synthesized in Example 6 and "91-99·2F-Y" (SEQ ID No: 40) synthesized in Example 9, as well as the above "84-92" (SEQ ID NO: 1) and "84-92·2F-Y" (SEQ ID NO: 39). The results are shown in Table 7.

TABLE 7

| Antigen Peptide | IFN-γ in Supernatant (pg/ml) | |
|---|---|---|
| | BEC-2 | Ban-B1 |
| "84-92" | 1896 | 160 |
| "84-92 · 2F-Y" | 710 | 46 |
| "91-99" | >2000 | 40 |
| "91-99 · 2F-Y" | 650 | 100 |

Peripheral blood lymphocytes stimulated with "84-92", "84-92·2F-Y", "91-99", and "91-99·2F-Y" peptides reacted to HLA-A24-positive BEC-2 but not to HLA-A24-negative Ban-B 1, indicating induction of HLA-A24-restricted tumor antigen peptide-specific CTLs. Furthermore, peripheral blood lymphocytes stimulated with "84-92·2F-Y" and "91-99·2F-Y" peptides reacted to BEC-2 as with the peripheral blood lymphocytes stimulated with "84-92" and "91-99" peptides, indicating that the derivatives obtained from the original peptides by substitution had CTL-inducing ability similar to that of the original peptide.

Likewise, a similar experiment can be conducted wherein COS-7 cells (ATCC No. CRL1651) or VA-13 cells (RIKEN CELL BANK, The Institute of Physical and Chemical Research) into which an expression plasmid for HLA-A2402 cDNA (GenBank Accession No. M64740) has been introduced and which have been pulsed with the above peptides are substituted for BEC-2 used in the above experiment, and COS-7 or VA-13 cells into which the expression plasmid for HLA-A2402 cDNA has been introduced but which have not been pulsed with the peptides are substituted for Ban-B 1 used in the above experiment (*J. Exp. Med.*, 187:277, 1998).

EXAMPLE 11

Synthesis of Cyclophilin-Derived Peptides

Since it was revealed from the above-described Examples 1-10 that cyclophilin B is a tumor antigen protein, the present inventors also investigated whether cyclophilins A, C, and D, known as homologs of cyclophilin B, have also such activity.

The amino acid sequences of cyclophilins A, C, and D have also been published (*Biochemistry*, 3:8218, 1994). Based on the literature, three peptides having a binding motif for HLA-A24, that is, a peptide comprising a sequence from position 59 to position 67 of the amino acid sequence of cyclophilin A (SEQ ID NO: 41, hereinafter sometimes referred to as Cyp-A"59-67"), a peptide comprising a sequence from position 89 to position 97 of the amino acid sequence of cyclophilin C (SEQ ID NO: 42, hereinafter sometimes referred to as Cyp-C"89-97"), and a peptide comprising a sequence from position 94 to position 102 of the amino acid sequence of cyclophilin D (SEQ ID NO: 43, hereinafter sometimes referred to as Cyp-D"94-102") were selected and synthesized by the Fmoc method. As an example, synthesis of Cyp-A"59-67" (SEQ ID NO: 41) and its result are described below.

Fmoc-Phe-Alko Resin (0.67 mmol/g, 100-200 mesh) was used as a resin in this synthesis. Using 50 mg of this resin, the synthesis was started according to Schedule 1 described below (Table 8) to couple the following residues in order: Fmoc-Asp(OtBu)-OH, Fmoc-Gly-OH, Fmoc-Gly-OH, Fmoc-Gln-OH, Fmoc-Cys(Trt)-OH, Fmoc-Met-OH, Fmoc-Phe-OH, and Fmoc-Gly-OH. After the coupling, the procedures were carried out up to Step 3 of Schedule 1 (Table 8) to obtain a peptide resin.

To this peptide resin, 1 ml of Reagent K (5% phenol, 5% thioanisole, 5% $H_2O$, and 2.5% ethanedithiol in TFA) was added and allowed to react for 2.5 hours at room temperature. While cooling with ice, 10 ml of diethyl ether was added to the reaction, the mixture was stirred for 10 minutes, filtered, and then washed with 10 ml of diethyl ether. To the filter cake, 10 ml of aqueous acetic acid was added and the mixture was stirred for 30 minutes. The resin was then filtered, and washed with 4 ml of aqueous acetic acid. After lyophilizing the filtrate and the wash, the crude peptide obtained was dissolved in aqueous acetic acid, and injected into a reverse phase packing material YMC-PACK ODS-A SH-363-5 (30φ×250 mm) pre-equilibrated with 0.1% aqueous TFA. The column was washed with 0.1% aqueous TFA, and the concentration of acetonitrile was then increased from 0 to 15% over 60 minutes and from 15% to 30% over 240 minutes to elute the product at a flow rate of 7 ml/min. The eluate was monitored by A 220 nm. The fractions containing the desired product were combined together and lyophilized to obtain 9.7 mg of Gly-Phe-Met-Cys-Gln-Gly-Gly-Asp-Phe (SEQ ID NO:41).

The peptide obtained, Gly-Phe-Met-Cys-Gln-Gly-Gly-Asp-Phe (SEQ ID NO:41), was analyzed using a reverse phase packing material YMC-PACK ODS-AM AM303 (4.6φ×250 mm), and proved to have a retention time of 18.8 minutes with a linear gradient of acetonitrile concentration from 18% to 48% containing 0.1% TFA. The results of amino acid analysis (Cys could not be detected) and mass spectrometry of the product were consistent with the theoretical values.

Amino Acid Analysis

Hydrolysis: 1% phenol/6N aqueous hydrochloric acid, 110° C., 10 hours;

Analysis method: the ninhydrin method;

* Reference amino acid; Theoretical values are indicated in parentheses:

Asx: 0.99 (1)

Glx: 1.06 (1)

Gly: 2.96 (3)

Met: 0.99 (1)

*Phe: 2.00 (2)

Mass Spectrum (FAB)

$[M+H]^+$: 961

TABLE 8

Schedule 1

| Step | Duration (min) × the number of treatments |
|---|---|
| 1. (washing) DMF 1.2 ml | 1 × 2 |
| 2. (deprotection) 50% piperidine/DMF | 12 × 1 |
| 3. (washing) DMF 1.2 ml | 1 × 7 |
| 4. (coupling) each amino-protected amino acid (5 equivalents)/NMP solution 0.9 ml, DIC (5 equivalents)/NMP solution 0.3 ml | 30 × 1 |
| 5. (washing) DMF 1.2 ml | 1 × 2 |
| 6. (coupling) each amino-protected amino acid (5 equivalents)/NMP solution 0.9 ml, DIC (5 equivalents)/NMP solution 0.3 ml | 30 × 1 |
| 7. (washing) DMF 1.2 ml | 1 × 4 |

EXAMPLE 12

Induction of CTL from Peripheral Blood Lymphocytes by Cyclophilin-Derived Peptides The inventors investigated whether the three peptides synthesized in Example 11 can be used to induce antigen-specific CTLs from peripheral blood lymphocytes. Lymphocytes were separated from peripheral blood of a healthy donor who was homozygous for A24 in the HLA-A locus using Ficoll method. The lymphocytes were stimulated three times with the above peptides in the same manner as that described in Example 10. The lymphocytes were harvested one week after the third stimulation, and measured for their cytotoxic activity using $^{51}Cr$-labeled, HLA-A24-positive, T cell lymphoma-derived cell line KOPT-K1 and HLA-A24-negative, T cell leukemia-derived cell line RPMI8402 as target cells, according to the method described in D. D. Kharkevitch et al., *Int. J. Cancer*, 58:317 (1994). The results are shown in Table 9.

TABLE 9

| | Cytotoxic Activity against Target Cell (%) | |
|---|---|---|
| Stimulator Peptide | KOPT-K1 | RPMI8402 |
| Cyp-A"59-67" | 27 | 0 |
| Cyp-C"89-97" | 20 | 0 |
| Cyp-D"94-102" | 22 | 0 |

The lymphocytes stimulated with Crp-A"59-67", Crp-C"89-97"", and Cryp-D"94-102" peptides reacted to HLA-A24-positive KOPT-K1 but not to HLA-A24-negative RPMI8402, indicating induction of HLA-A24-restricted, tumor antigen peptide-specific CTLs. It was demonstrated by the above results that cyclophilins other than cyclophilin B also function as a tumor antigen.

Likewise, a similar experiment can be conducted wherein recombinant cells described at the end of Example 10 are substituted for KOPT-K1 and RPMI8402 used in this experiment.

EXAMPLE 13

Induction of CTL from Peripheral Blood Lymphocytes by Cyclophilin Protein

By referring to the methods described in the literature (e.g., *J. Immunol.*, 158:1796, 1997 and *Cancer Res.*, 59:1184, 1999), appropriate cells may be pulsed with a cyclophilin of the present invention, a partial polypeptide thereof, a cyclophilin-derived tumor antigen peptide of the present invention, or the like, to prepare antigen-presenting cells on which a complex between an HLA antigen and a cyclophilin-derived tumor antigen peptide is presented. Successful preparation of desired antigen-presenting cells can be confirmed by determining whether antigen-specific CTLs are induced from peripheral blood lymphocytes by the antigen-presenting cells. Although the following descriptions indicate an example in which peripheral blood from a healthy donor is used, it goes without saying that antigen-presenting cells can also be prepared in a similar manner using peripheral blood from a tumor patient.

Lymphocytes are firstly separated by Ficoll method from 2) peripheral blood of an HLA-A24-positive healthy donor. The lymphocytes are allowed to stand for 3 hours in a culture flask at 37° C. to remove non-adherent cells. The adherent cells are cultured for 7 days in the presence of GM-CSF (2000 U/ml) and IL-4 (2000 U/ml) to induce dendritic cells, which is known to have high antigen-presenting ability. Harvested dendritic cells are cultured with 10 µg/ml tumor antigen peptide of the present invention, or 100 µg/ml tumor antigen protein (cyclophilin) of the present invention or partial polypeptide thereof at 37° C. for 2 hours to be pulsed, and then irradiated with X-ray (5000 rad). In a 24-well plate, the dendritic cells pulsed with the above peptide or protein are co-cultured with CD8+ T cell prepared using biomagnetic separation beads (Dynal) from peripheral blood lymphocytes of the above healthy donor for antigenic stimulation. On the day following the stimulation, IL-2 (100 U/ml) is added. T cells are stimulated every week (2 to 4 times) in the same manner using the above dendritic cells pulsed with the peptide or protein. One week after the last stimulation, cultured T cells are harvested. Using as target cells BEC-2, which is an HLA-A2402-positive EB virus-transformed B cell line expressing the tumor antigen protein of the present invention, and Ban-B1, which is an HLA-A2402-negative EB virus-transformed B cell line expressing the tumor antigen protein of the present invention, the reactivity of the above T cells is determined by measuring the amount of IFN-γ in the culture supernatant by ELISA as in Example 10 or by measuring cytotoxic activity on $^{51}$Cr-labeled target cells. Where antigen-specific CTLs has been induced, the reaction is observed only against BEC-2. By conducting the above experiment, one can determine whether antigen-presenting cells (dendritic cells) pulsed with the tumor antigen peptide, tumor antigen protein of the present invention, or the like have activity of inducing antigen-specific CTLs.

Likewise, a similar experiment can be conducted wherein COS-7 cells (ATCC No. CRL1651) or VA-13 cells (RIKEN CELL BANK, The Institute of Physical and Chemical Research) into which an expression plasmid for HLA-A2402 cDNA (GenBank Accession No. M64740) has been introduced and which have been pulsed with a tumor antigen peptide or tumor antigen protein of the present invention are substituted for BEC-2 used in the above experiment, and COS-7 or VA-13 cells into which the expression plasmid for HLA-A2402 cDNA has been introduced but which have not been pulsed with the above peptide or the like are substituted for Ban-B 1 used in the above experiment (*J. Exp. Med.*, 187:277, 1998).

Sequence Listing Free Text

In the amino acid sequence shown in SEQ ID NO: 37, the second amino acid is phenylalanine, tyrosine, methionine, or tryptophan, and the ninth amino acid is phenylalanine, leucine, isoleucine, tryptophan, or methionine.

In the amino acid sequence shown in SEQ ID NO: 38, the second amino acid is phenylalanine, tyrosine, methionine, or tryptophan, and the ninth amino acid is phenylalanine, leucine, isoleucine, tryptophan, or methionine.

INDUSTRIAL APPLICABILITY

According to the present invention, tumor antigen peptides derived from cyclophilins and derivatives thereof having the functionally equivalent properties can be provided, as well as medicaments, prophylactics, or diagnostics for tumors using such tumor antigen peptides, derivatives thereof, cyclophilin polypeptides, or genes therefor in vivo or in vitro.

The invention claimed is:

1. An isolated dendritic cell wherein a complex between an HLA-A24 antigen and a tumor antigen peptide consisting of a sequence selected from the group consisting of: SEQ ID NO: 1, SEQ ID: NO 2, SEQ ID NO: 39, SEQ ID NO: 40, SEQ ID NO: 41, SEQ ID NO: 42, and SEQ ID NO: 43, is presented on the surface.

2. The dendritic cell of claim 1 in which the HLA-A24 antigen-tumor antigen peptide complex is recognized by a cytotoxic T lymphocyte.

3. A composition comprising the dendritic cell of claim 1.

4. A composition comprising the dendritic cell of claim 2.

* * * * *

UNITED STATES PATENT AND TRADEMARK OFFICE
CERTIFICATE OF CORRECTION

PATENT NO. : 7,368,107 B2 Page 1 of 1
APPLICATION NO. : 11/227238
DATED : May 6, 2008
INVENTOR(S) : Kyogo Itoh et al.

It is certified that error appears in the above-identified patent and that said Letters Patent is hereby corrected as shown below:

On the Title page, item [73]

"Assignee: Dainippon Sumitomo Pharma Co., Ltd." should read
--Assignee: Kyogo ITOH, Miyaki-gun (JP); Dainippon Sumitomo Pharma Co., Ltd., Osaka (JP).--

Signed and Sealed this

Eighteenth Day of November, 2008

JON W. DUDAS
*Director of the United States Patent and Trademark Office*

SEQUENCE LISTING

```
<160> NUMBER OF SEQ ID NOS: 44

<210> SEQ ID NO 1
<211> LENGTH: 9
<212> TYPE: PRT
<213> ORGANISM: Homo sapiens

<400> SEQUENCE: 1

Lys Phe His Arg Val Ile Lys Asp Phe
1               5

<210> SEQ ID NO 2
<211> LENGTH: 9
<212> TYPE: PRT
<213> ORGANISM: Homo sapiens
```

```
<400> SEQUENCE: 2

Asp Phe Met Ile Gln Gly Gly Asp Phe
1               5

<210> SEQ ID NO 3
<211> LENGTH: 9
<212> TYPE: PRT
<213> ORGANISM: Homo sapiens

<400> SEQUENCE: 3

Gly Phe Gly Tyr Lys Asn Ser Lys Phe
1               5

<210> SEQ ID NO 4
<211> LENGTH: 11
<212> TYPE: PRT
<213> ORGANISM: Homo sapiens

<400> SEQUENCE: 4

Gly Tyr Lys Asn Ser Lys Phe His Arg Val Ile
1               5                   10

<210> SEQ ID NO 5
<211> LENGTH: 11
<212> TYPE: PRT
<213> ORGANISM: Homo sapiens

<400> SEQUENCE: 5

Asn Phe Lys Leu Lys His Tyr Gly Pro Gly Trp
1               5                   10

<210> SEQ ID NO 6
<211> LENGTH: 11
<212> TYPE: PRT
<213> ORGANISM: Homo sapiens

<400> SEQUENCE: 6

Ile Tyr Gly Glu Arg Phe Pro Asp Glu Asn Phe
1               5                   10

<210> SEQ ID NO 7
<211> LENGTH: 9
<212> TYPE: PRT
<213> ORGANISM: Homo sapiens

<400> SEQUENCE: 7

Arg Phe Pro Asp Glu Asn Phe Lys Leu
1               5

<210> SEQ ID NO 8
<211> LENGTH: 9
<212> TYPE: PRT
<213> ORGANISM: Homo sapiens

<400> SEQUENCE: 8

His Tyr Gly Pro Gly Trp Val Ser Met
1               5

<210> SEQ ID NO 9
<211> LENGTH: 10
<212> TYPE: PRT
<213> ORGANISM: Homo sapiens

<400> SEQUENCE: 9
```

-continued

```
Phe Phe Ile Thr Thr Val Lys Thr Ala Trp
1               5                   10

<210> SEQ ID NO 10
<211> LENGTH: 10
<212> TYPE: PRT
<213> ORGANISM: Homo sapiens

<400> SEQUENCE: 10

Ala Trp Leu Asp Gly Lys His Val Val Phe
1               5                   10

<210> SEQ ID NO 11
<211> LENGTH: 9
<212> TYPE: PRT
<213> ORGANISM: Homo sapiens

<400> SEQUENCE: 11

Val Phe Gly Lys Val Leu Glu Gly Met
1               5

<210> SEQ ID NO 12
<211> LENGTH: 8
<212> TYPE: PRT
<213> ORGANISM: Homo sapiens

<400> SEQUENCE: 12

Lys Val Leu Leu Ala Ala Ala Leu
1               5

<210> SEQ ID NO 13
<211> LENGTH: 11
<212> TYPE: PRT
<213> ORGANISM: Homo sapiens

<400> SEQUENCE: 13

Leu Leu Ala Ala Ala Leu Ile Ala Gly Ser Val
1               5                   10

<210> SEQ ID NO 14
<211> LENGTH: 10
<212> TYPE: PRT
<213> ORGANISM: Homo sapiens

<400> SEQUENCE: 14

Ala Leu Ile Ala Gly Ser Val Phe Phe Leu
1               5                   10

<210> SEQ ID NO 15
<211> LENGTH: 11
<212> TYPE: PRT
<213> ORGANISM: Homo sapiens

<400> SEQUENCE: 15

Ala Leu Ile Ala Gly Ser Val Phe Phe Leu Leu
1               5                   10

<210> SEQ ID NO 16
<211> LENGTH: 9
<212> TYPE: PRT
<213> ORGANISM: Homo sapiens

<400> SEQUENCE: 16

Leu Ile Ala Gly Ser Val Phe Phe Leu
1               5
```

<210> SEQ ID NO 17
<211> LENGTH: 10
<212> TYPE: PRT
<213> ORGANISM: Homo sapiens

<400> SEQUENCE: 17

Leu Ile Ala Gly Ser Val Phe Phe Leu Leu
1               5                   10

<210> SEQ ID NO 18
<211> LENGTH: 11
<212> TYPE: PRT
<213> ORGANISM: Homo sapiens

<400> SEQUENCE: 18

Leu Ile Ala Gly Ser Val Phe Phe Leu Leu Leu
1               5                   10

<210> SEQ ID NO 19
<211> LENGTH: 10
<212> TYPE: PRT
<213> ORGANISM: Homo sapiens

<400> SEQUENCE: 19

Lys Val Thr Val Lys Val Tyr Phe Asp Leu
1               5                   10

<210> SEQ ID NO 20
<211> LENGTH: 8
<212> TYPE: PRT
<213> ORGANISM: Homo sapiens

<400> SEQUENCE: 20

Thr Val Lys Val Tyr Phe Asp Leu
1               5

<210> SEQ ID NO 21
<211> LENGTH: 9
<212> TYPE: PRT
<213> ORGANISM: Homo sapiens

<400> SEQUENCE: 21

Asp Leu Arg Ile Gly Asp Glu Asp Val
1               5

<210> SEQ ID NO 22
<211> LENGTH: 9
<212> TYPE: PRT
<213> ORGANISM: Homo sapiens

<400> SEQUENCE: 22

Asp Val Gly Arg Val Ile Phe Gly Leu
1               5

<210> SEQ ID NO 23
<211> LENGTH: 11
<212> TYPE: PRT
<213> ORGANISM: Homo sapiens

<400> SEQUENCE: 23

Arg Val Ile Phe Gly Leu Phe Gly Lys Thr Val
1               5                   10

```
<210> SEQ ID NO 24
<211> LENGTH: 11
<212> TYPE: PRT
<213> ORGANISM: Homo sapiens

<400> SEQUENCE: 24

Gly Leu Phe Gly Lys Thr Val Pro Lys Thr Val
1               5                   10

<210> SEQ ID NO 25
<211> LENGTH: 10
<212> TYPE: PRT
<213> ORGANISM: Homo sapiens

<400> SEQUENCE: 25

Thr Val Pro Lys Thr Val Asp Asn Phe Val
1               5                   10

<210> SEQ ID NO 26
<211> LENGTH: 8
<212> TYPE: PRT
<213> ORGANISM: Homo sapiens

<400> SEQUENCE: 26

Thr Val Asp Asn Phe Val Ala Leu
1               5

<210> SEQ ID NO 27
<211> LENGTH: 10
<212> TYPE: PRT
<213> ORGANISM: Homo sapiens

<400> SEQUENCE: 27

Lys Leu Lys His Tyr Gly Pro Gly Trp Val
1               5                   10

<210> SEQ ID NO 28
<211> LENGTH: 8
<212> TYPE: PRT
<213> ORGANISM: Homo sapiens

<400> SEQUENCE: 28

Ser Gln Phe Phe Ile Thr Thr Val
1               5

<210> SEQ ID NO 29
<211> LENGTH: 10
<212> TYPE: PRT
<213> ORGANISM: Homo sapiens

<400> SEQUENCE: 29

Phe Ile Thr Thr Val Lys Thr Ala Trp Leu
1               5                   10

<210> SEQ ID NO 30
<211> LENGTH: 8
<212> TYPE: PRT
<213> ORGANISM: Homo sapiens

<400> SEQUENCE: 30

Trp Leu Asp Gly Lys His Val Val
1               5

<210> SEQ ID NO 31
<211> LENGTH: 8
```

```
<212> TYPE: PRT
<213> ORGANISM: Homo sapiens

<400> SEQUENCE: 31

His Val Val Phe Gly Lys Val Leu
1               5

<210> SEQ ID NO 32
<211> LENGTH: 8
<212> TYPE: PRT
<213> ORGANISM: Homo sapiens

<400> SEQUENCE: 32

Lys Val Leu Glu Gly Met Glu Val
1               5

<210> SEQ ID NO 33
<211> LENGTH: 9
<212> TYPE: PRT
<213> ORGANISM: Homo sapiens

<400> SEQUENCE: 33

Lys Val Leu Glu Gly Met Glu Val Val
1               5

<210> SEQ ID NO 34
<211> LENGTH: 8
<212> TYPE: PRT
<213> ORGANISM: Homo sapiens

<400> SEQUENCE: 34

Val Leu Glu Gly Met Glu Val Val
1               5

<210> SEQ ID NO 35
<211> LENGTH: 11
<212> TYPE: PRT
<213> ORGANISM: Homo sapiens

<400> SEQUENCE: 35

Val Leu Glu Gly Met Glu Val Val Arg Lys Val
1               5                   10

<210> SEQ ID NO 36
<211> LENGTH: 8
<212> TYPE: PRT
<213> ORGANISM: Homo sapiens

<400> SEQUENCE: 36

Gly Met Glu Val Val Arg Lys Val
1               5

<210> SEQ ID NO 37
<211> LENGTH: 9
<212> TYPE: PRT
<213> ORGANISM: Artificial Sequence
<220> FEATURE:
<223> OTHER INFORMATION: Variant of SEQ ID NO:1
<220> FEATURE:
<221> NAME/KEY: misc_feature
<222> LOCATION: (2)..(2)
<223> OTHER INFORMATION: Xaa is Phe, Tyr, Met or Trp
<220> FEATURE:
<221> NAME/KEY: misc_feature
<222> LOCATION: (9)..(9)
<223> OTHER INFORMATION: Xaa is Phe, Leu, Ile, Trp or Met
```

```
<400> SEQUENCE: 37

Lys Xaa His Arg Val Ile Lys Asp Xaa
1               5

<210> SEQ ID NO 38
<211> LENGTH: 9
<212> TYPE: PRT
<213> ORGANISM: Artificial Sequence
<220> FEATURE:
<223> OTHER INFORMATION: Variant of SEQ ID NO:2
<220> FEATURE:
<221> NAME/KEY: misc_feature
<222> LOCATION: (2)..(2)
<223> OTHER INFORMATION: Xaa is Phe, Tyr, Met or Trp
<220> FEATURE:
<221> NAME/KEY: misc_feature
<222> LOCATION: (9)..(9)
<223> OTHER INFORMATION: Xaa is Phe, Leu, Ile, Trp or Met

<400> SEQUENCE: 38

Asp Xaa Met Ile Gln Gly Gly Asp Xaa
1               5

<210> SEQ ID NO 39
<211> LENGTH: 9
<212> TYPE: PRT
<213> ORGANISM: Artificial Sequence
<220> FEATURE:
<223> OTHER INFORMATION: Variant of SEQ ID NO:1

<400> SEQUENCE: 39

Lys Tyr His Arg Val Ile Lys Asp Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Variant of SEQ ID NO:2

<400> SEQUENCE: 40

Asp Tyr Met Ile Gln Gly Gly Asp Phe
1               5

<210> SEQ ID NO 41
<211> LENGTH: 9
<212> TYPE: PRT
<213> ORGANISM: Homo sapiens

<400> SEQUENCE: 41

Gly Phe Met Cys Gln Gly Gly Asp Phe
1               5

<210> SEQ ID NO 42
<211> LENGTH: 9
<212> TYPE: PRT
<213> ORGANISM: Homo sapiens

<400> SEQUENCE: 42

Asp Phe Met Ile Gln Gly Gly Asp Ile
1               5

<210> SEQ ID NO 43
<211> LENGTH: 9
<212> TYPE: PRT
<213> ORGANISM: Homo sapiens
```

```
<400> SEQUENCE: 43

Thr Phe His Arg Val Ile Pro Ser Phe
1               5

<210> SEQ ID NO 44
<211> LENGTH: 208
<212> TYPE: PRT
<213> ORGANISM: Homo sapiens

<400> SEQUENCE: 44

Met Lys Val Leu Leu Ala Ala Ala Leu Ile Ala Gly Ser Val Phe Phe
1               5                   10                  15

Leu Leu Leu Pro Gly Pro Ser Ala Ala Asp Glu Lys Lys Lys Gly Pro
                20                  25                  30

Lys Val Thr Val Lys Val Tyr Phe Asp Leu Arg Ile Gly Asp Glu Asp
            35                  40                  45

Val Gly Arg Val Ile Phe Gly Leu Phe Gly Lys Thr Val Pro Lys Thr
    50                  55                  60

Val Asp Asn Phe Val Ala Leu Ala Thr Gly Glu Lys Gly Phe Gly Tyr
65                  70                  75                  80

Lys Asn Ser Lys Phe His Arg Val Ile Lys Asp Phe Met Ile Gln Gly
                85                  90                  95

Gly Asp Phe Thr Arg Gly Asp Gly Thr Gly Gly Lys Ser Ile Tyr Gly
                100                 105                 110

Glu Arg Phe Pro Asp Glu Asn Phe Lys Leu Lys His Tyr Gly Pro Gly
            115                 120                 125

Trp Val Ser Met Ala Asn Ala Gly Lys Asp Thr Asn Gly Ser Gln Phe
    130                 135                 140

Phe Ile Thr Thr Val Lys Thr Ala Trp Leu Asp Gly Lys His Val Val
145                 150                 155                 160

Phe Gly Lys Val Leu Glu Gly Met Glu Val Val Arg Lys Val Glu Ser
                165                 170                 175

Thr Lys Thr Asp Ser Arg Asp Lys Pro Leu Lys Asp Val Ile Ile Ala
            180                 185                 190

Asp Cys Gly Lys Ile Glu Val Glu Lys Pro Phe Ala Ile Ala Lys Glu
        195                 200                 205
```